US009060944B2

(12) United States Patent
Charrier et al.

(10) Patent No.: US 9,060,944 B2
(45) Date of Patent: *Jun. 23, 2015

(54) COSMETIC COMPOSITION RICH IN FATTY SUBSTANCES COMPRISING A POLYOXYALKYLENATED FATTY ALCOHOL ETHER AND A DIRECT DYE AND/OR AN OXIDATION DYE, THE DYEING METHOD AND THE DEVICE

(75) Inventors: Delphine Charrier, Boulogne Billancourt (FR); Evelyne Vacherand, Eaubonne (FR); Marie-Pascale Audousset, Asnieres (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/130,800

(22) PCT Filed: Jul. 5, 2012

(86) PCT No.: PCT/EP2012/063097
§ 371 (c)(1),
(2), (4) Date: Apr. 4, 2014

(87) PCT Pub. No.: WO2013/004773
PCT Pub. Date: Jan. 10, 2013

(65) Prior Publication Data
US 2014/0215728 A1 Aug. 7, 2014

Related U.S. Application Data

(60) Provisional application No. 61/523,903, filed on Aug. 16, 2011, provisional application No. 61/523,907, filed on Aug. 16, 2011.

(30) Foreign Application Priority Data

Jul. 5, 2011 (FR) ...................................... 11 56074
Jul. 5, 2011 (FR) ...................................... 11 56075

(51) Int. Cl.
*A61Q 5/10* (2006.01)
*A61K 8/34* (2006.01)
*A61K 8/31* (2006.01)
*A61Q 5/06* (2006.01)
*A61K 8/86* (2006.01)
*A61K 8/39* (2006.01)

(52) U.S. Cl.
CPC . *A61K 8/342* (2013.01); *A61K 8/31* (2013.01); *A61Q 5/06* (2013.01); *A61Q 5/10* (2013.01); *A61K 8/86* (2013.01); *A61K 8/39* (2013.01)

(58) Field of Classification Search
CPC ............. A61Q 5/10; A61Q 5/06; A61K 8/39; A61K 8/86; A61K 8/342; A61K 2800/882
USPC ............. 8/405, 406, 410, 412, 462, 552, 554, 8/594, 619
See application file for complete search history.

(56) References Cited

U.S. PATENT DOCUMENTS

| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,100,739 A | 8/1963 | Kaiser et al. |

(Continued)

FOREIGN PATENT DOCUMENTS

| CA | 1069522 A1 | 1/1980 |
| DE | 2359399 A1 | 6/1975 |

(Continued)

OTHER PUBLICATIONS

STIC Search Report Dated Aug. 12, 2014.*
International Search Report for PCT/EP2012/063097.
Todd, Charles et al., "Volatile Silicone Fluids for Cosmetic Formulations," Cosmetics and Toiletries, vol. 91, Jan. 1976, pp. 29-32.
Porter, M.R., "Handbook of Surfactants," published by Chapman and Hall, NY, 1991, pp. 116-178.
International Search Report for co-pending application PCT/EP2012/063090.
International Search Report for co-pending application PCT/EP2012/063154.
Non-Final Office Action dated Aug. 20, 2014, for co-pending U.S. Appl. No. 14/130,795, entitled "Dye Composition Using a Long-Chain Ether of an Alkoxylated Fatty Alcohol and a Cationic Polymer, Processes and Devices Using the Same," filed Apr. 4, 2014.
Non-Final Office Action dated Aug. 20, 2014, for co-pending U.S. Appl. No. 14/130,846, entitled "Dye Composition Comprising an Alkoxylated Fatty Alcohol Ether and a Fatty Alcohol," filed Apr. 4, 2014.

*Primary Examiner* — Eisa Elhilo
(74) *Attorney, Agent, or Firm* — The Marbury Law Group, PLLC

(57) ABSTRACT

A subject-matter of the present invention is a composition for dyeing keratin fibers, in particular human keratin fibers such as the hair, comprising: i) at least one non-ionic ether of polyoxyalkylenated fatty alcohols of formula (I), and also the optical isomers and geometrical isomers thereof; in which formula (I): R denotes a saturated or unsaturated and linear or branched $C_{10}$-$C_{30}$ hydrocarbon radical, R' denotes a saturated or unsaturated and linear or branched $C_{10}$-$C_{30}$ hydrocarbon radical, which may be substituted by a hydroxyl radical, n is an integer between (1) and approximately (100) inclusive, and Alk represents a linear or branched, preferably linear, ($C_1$-$C_6$) alkylene group such as ethylene or propylene, preferably ethylene, ii) at least one fatty substance, iii) optionally at least one surfactant other than i), iv) at least one direct dye and/or at least one oxidation dye, v) optionally at least one basifying agent, vi) optionally at least one chemical oxidizing agent, and the fatty substance content of the composition representing in total at least 25% by weight relative to the total weight of the composition. The present invention also relates to a method using this composition and to a multi-compartment device that is suitable for the use of said method.

$$R\text{—}(O\text{-Alk})_n\text{—}O\text{—}R' \qquad (I)$$

26 Claims, No Drawings

(56) References Cited

U.S. PATENT DOCUMENTS

| | | |
|---|---|---|
| 3,206,462 A | 9/1965 | McCarty |
| 3,227,615 A | 1/1966 | Korden |
| 3,472,840 A | 10/1969 | Stone et al. |
| 3,524,842 A | 8/1970 | Grossmann et al. |
| 3,578,386 A | 5/1971 | Kalopissis et al. |
| 3,589,978 A | 6/1971 | Kamal et al. |
| 3,617,163 A | 11/1971 | Kalopissis et al. |
| 3,632,559 A | 1/1972 | Matter et al. |
| 3,665,036 A | 5/1972 | Kalopissis et al. |
| 3,817,698 A | 6/1974 | Kalopissis et al. |
| 3,867,456 A | 2/1975 | Kalopissis et al. |
| 3,869,454 A | 3/1975 | Lang et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,955,918 A | 5/1976 | Lang |
| 3,966,904 A | 6/1976 | Green et al. |
| 3,985,499 A | 10/1976 | Lang et al. |
| 3,986,825 A | 10/1976 | Sokol |
| 4,001,432 A | 1/1977 | Green et al. |
| 4,003,699 A | 1/1977 | Rose et al. |
| 4,005,193 A | 1/1977 | Green et al. |
| 4,013,787 A | 3/1977 | Varlerberghe et al. |
| 4,025,301 A | 5/1977 | Lang |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,137,180 A | 1/1979 | Naik et al. |
| 4,151,162 A | 4/1979 | Lang et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| RE30,199 E | 1/1980 | Rose et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,226,784 A | 10/1980 | Kalopissis et al. |
| 4,240,450 A | 12/1980 | Grollier et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,390,689 A | 6/1983 | Jacquet et al. |
| 4,422,853 A | 12/1983 | Jacquet et al. |
| 4,445,521 A | 5/1984 | Grollier et al. |
| 4,555,246 A | 11/1985 | Grollier et al. |
| 4,579,732 A | 4/1986 | Grollier et al. |
| 4,591,610 A | 5/1986 | Grollier |
| 4,608,250 A | 8/1986 | Jacquet et al. |
| 4,645,663 A | 2/1987 | Grollier |
| 4,702,906 A | 10/1987 | Jacquet et al. |
| 4,719,099 A | 1/1988 | Grollier et al. |
| 4,719,282 A | 1/1988 | Nadolsky et al. |
| 4,761,273 A | 8/1988 | Grollier et al. |
| 4,777,040 A | 10/1988 | Grollier et al. |
| 4,839,166 A | 6/1989 | Grollier et al. |
| 4,874,554 A | 10/1989 | Lange et al. |
| 4,886,517 A | 12/1989 | Bugaut et al. |
| 4,948,579 A | 8/1990 | Jacquet et al. |
| 4,970,066 A | 11/1990 | Grollier et al. |
| 4,996,059 A | 2/1991 | Grollier et al. |
| 5,009,880 A | 4/1991 | Grollier et al. |
| 5,061,289 A | 10/1991 | Clausen et al. |
| 5,089,252 A | 2/1992 | Grollier et al. |
| 5,196,189 A | 3/1993 | Jacquet et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Mockli |
| 5,766,576 A | 6/1998 | Lowe et al. |
| 5,879,413 A | 3/1999 | Pengilly et al. |
| 5,888,252 A | 3/1999 | Mockli |
| 5,919,273 A | 7/1999 | Rondeau et al. |
| 5,958,392 A | 9/1999 | Grollier et al. |
| 5,993,490 A | 11/1999 | Rondeau et al. |
| 6,045,591 A | 4/2000 | Deneulenaere |
| 6,099,592 A | 8/2000 | Vidal et al. |
| 6,136,042 A | 10/2000 | Maubru |
| 6,179,881 B1 | 1/2001 | Henrion et al. |
| 6,284,003 B1 | 9/2001 | Rose et al. |
| 6,338,741 B1 | 1/2002 | Vidal et al. |
| 6,436,151 B2 | 8/2002 | Cottard et al. |
| 6,451,069 B2 | 9/2002 | Matsunaga et al. |
| 6,492,502 B2 | 12/2002 | Henrion et al. |
| 6,645,258 B2 | 11/2003 | Vidal et al. |
| 6,695,887 B2 | 2/2004 | Cottard et al. |
| 6,730,789 B1 | 5/2004 | Birault et al. |
| 6,797,013 B1 | 9/2004 | Lang et al. |
| 6,863,883 B1 | 3/2005 | Tsujino et al. |
| 7,927,383 B2 | 4/2011 | Hercouet et al. |
| 8,088,173 B2 | 1/2012 | Debain et al. |
| 2001/0001332 A1 | 5/2001 | Henrion et al. |
| 2001/0023515 A1 | 9/2001 | Cottard et al. |
| 2001/0032368 A1* | 10/2001 | Bone et al. ......... 8/405 |
| 2001/0044975 A1 | 11/2001 | Mastunaga et al. |
| 2002/0010970 A1 | 1/2002 | Cottard et al. |
| 2002/0050013 A1 | 5/2002 | Vidal et al. |
| 2002/0165368 A1 | 11/2002 | Henrion et al. |
| 2002/0184717 A9 | 12/2002 | Cottard et al. |
| 2003/0019051 A9 | 1/2003 | Vidal et al. |
| 2004/0234471 A1 | 11/2004 | Corbella et al. |
| 2006/0248662 A1 | 11/2006 | Legrand |
| 2007/0101513 A1 | 5/2007 | Javet et al. |
| 2008/0216253 A1* | 9/2008 | Noecker et al. ......... 8/407 |
| 2009/0151089 A1 | 6/2009 | Audousset |
| 2010/0154136 A1* | 6/2010 | Hercouet et al. ......... 8/406 |
| 2010/0180389 A1 | 7/2010 | Hercouet et al. |
| 2011/0126363 A1 | 6/2011 | Debain et al. |

FOREIGN PATENT DOCUMENTS

| | | |
|---|---|---|
| DE | 2527638 | 5/1976 |
| DE | 2538363 A1 | 5/1976 |
| DE | 3843892 A1 | 6/1990 |
| DE | 4133957 A1 | 4/1993 |
| DE | 4137005 A1 | 5/1993 |
| DE | 4220388 A1 | 12/1993 |
| DE | 19543988 A1 | 5/1997 |
| DE | 10129034 A1 | 12/2002 |
| EP | 0080976 A1 | 6/1983 |
| EP | 0122324 A1 | 10/1984 |
| EP | 0337354 A1 | 10/1989 |
| EP | 0714954 A2 | 6/1996 |
| EP | 0770375 A1 | 5/1997 |
| EP | 0850636 A1 | 7/1998 |
| EP | 0850637 A1 | 7/1998 |
| EP | 0918053 A1 | 5/1999 |
| EP | 0920856 A1 | 6/1999 |
| EP | 1062940 A1 | 12/2000 |
| EP | 1106167 A2 | 6/2001 |
| EP | 1133975 A2 | 9/2001 |
| EP | 1133976 A2 | 9/2001 |
| EP | 2062615 A2 | 5/2009 |
| EP | 2198927 A2 | 6/2010 |
| FR | 1221122 A | 5/1960 |
| FR | 1492597 A | 8/1967 |
| FR | 1516943 A | 2/1968 |
| FR | 1540423 A | 8/1968 |
| FR | 1560664 A | 3/1969 |
| FR | 1567219 A | 5/1969 |
| FR | 1583363 A | 10/1969 |
| FR | 2077143 A | 10/1971 |
| FR | 2080759 A | 11/1971 |
| FR | 2162025 A1 | 7/1973 |

(56) References Cited

FOREIGN PATENT DOCUMENTS

| | | | |
|---|---|---|---|
| FR | 2189006 | A1 | 1/1974 |
| FR | 2190406 | A2 | 2/1974 |
| FR | 2252840 | A1 | 6/1975 |
| FR | 2270846 | A1 | 12/1975 |
| FR | 2275462 | A1 | 1/1976 |
| FR | 2280361 | A2 | 2/1976 |
| FR | 2285851 | A1 | 4/1976 |
| FR | 2316271 | A1 | 1/1977 |
| FR | 2320330 | A1 | 3/1977 |
| FR | 2336434 | A1 | 7/1977 |
| FR | 2368508 | A2 | 5/1978 |
| FR | 2383660 | A1 | 10/1978 |
| FR | 2393573 | A1 | 1/1979 |
| FR | 2413907 | A1 | 8/1979 |
| FR | 2470596 | A1 | 6/1981 |
| FR | 2502949 | A1 | 8/1981 |
| FR | 2505348 | A1 | 11/1982 |
| FR | 2519863 | A1 | 7/1983 |
| FR | 2542997 | A1 | 9/1984 |
| FR | 2570946 | A1 | 4/1986 |
| FR | 2598611 | A1 | 11/1987 |
| FR | 2733749 | A1 | 11/1996 |
| FR | 2757385 | A1 | 6/1998 |
| FR | 2788433 | A1 | 7/2000 |
| FR | 2801308 | A1 | 5/2001 |
| FR | 2803196 | A1 | 7/2001 |
| FR | 2803197 | A1 | 7/2001 |
| FR | 2923711 | A1 | 5/2009 |
| GB | 738585 | | 10/1955 |
| GB | 1026978 | A | 4/1966 |
| GB | 1153196 | A | 5/1969 |
| GB | 1195386 | A | 6/1970 |
| GB | 1331819 | A | 9/1973 |
| GB | 1514466 | A | 6/1978 |
| GB | 1546809 | A | 5/1979 |
| JP | 02019576 | | 1/1990 |
| JP | 5163124 | | 6/1993 |
| WO | 94/08969 | A1 | 4/1994 |
| WO | 94/08970 | A1 | 4/1994 |
| WO | 95/01772 | A1 | 1/1995 |
| WO | 95/15144 | A1 | 6/1995 |
| WO | 96/15765 | A1 | 5/1996 |
| WO | 97/44004 | A1 | 11/1997 |
| WO | 99/48465 | A1 | 9/1999 |
| WO | 01/66646 | A1 | 9/2001 |
| WO | 03/029359 | A1 | 4/2003 |
| WO | 2005/074873 | A1 | 8/2005 |
| WO | 2013/004772 | A2 | 1/2013 |
| WO | 2013/004784 | A2 | 1/2013 |

* cited by examiner

COSMETIC COMPOSITION RICH IN FATTY SUBSTANCES COMPRISING A POLYOXYALKYLENATED FATTY ALCOHOL ETHER AND A DIRECT DYE AND/OR AN OXIDATION DYE, THE DYEING METHOD AND THE DEVICE

CROSS REFERENCE TO RELATED APPLICATIONS

This is a national stage application of PCT/EP2012/063097, filed internationally on Jul. 5, 2012, which claims priority to U.S. Provisional Application Nos. 61/523,903 and 61/523,907, both filed on Aug. 16, 2011, as well as French Application Nos. FR 1156074 and FR 1156075, both filed on Jul. 5, 2011, all of which are incorporated herein by their entireties.

A subject-matter of the present invention is a composition for dyeing keratin fibres, comprising i) at least one non-ionic ether of polyoxyalkylenated fatty alcohol, ii) at least one fatty substance, iii) optionally at least one additional non-ionic surfactant other than i), iv) at least one direct dye and/or at least one oxidation dye, v) optionally at least one basifying agent and vi) optionally at least one chemical oxidizing agent, the fatty substance content of the composition representing in total at least 30% by weight, relative to the total weight of the composition.

The present invention also relates to a dyeing method using this composition, and to a multi-compartment device that is suitable for the use of this composition.

Among the methods for dyeing human keratin fibres, such as the hair, mention may be made of oxidation dyeing or permanent dyeing. More particularly, this form of dyeing uses one or more oxidation dyes, usually one or more oxidation bases optionally combined with one or more couplers.

In general, oxidation bases are chosen from ortho- or para-phenylenediamines, ortho- or para-aminophenols and heterocyclic compounds. These oxidation bases are colourless or weakly coloured compounds which, when combined with oxidizing products, can give access to coloured entities.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of molecules used as oxidation bases and couplers allows a rich palette of colours to be obtained.

It is also possible to add to these compositions direct dyes, which are coloured and colouring molecules having an affinity for the fibres. The direct dyes generally used are chosen from nitrobenzene, anthraquinone, nitropyridine, azo, methine, azomethine, xanthene, acridine, azine and triarylmethane direct dyes. The presence of such compounds enables the colouration obtained to be further enriched with tints or enables the chromaticity of the colouration obtained to be increased.

Oxidation dyeing methods thus consist in using, with these dyeing compositions, a composition comprising at least one oxidizing agent, generally hydrogen peroxide, under alkaline pH conditions in the vast majority of cases. The role of this oxidizing agent is to reveal the colouration, via an oxidative condensation reaction between the oxidation dyes.

The hair may also be coloured using solely direct dyes, such as those mentioned above. This direct dyeing can be carried out at acidic, neutral or alkaline pH and in the presence or absence of an oxidizing agent.

Dyeing, whether direct dyeing or oxidation dyeing, must moreover satisfy a certain number of requirements. Thus, it must be free of toxicological drawbacks, it must enable the desired shades to be obtained and it must show good resistance to external attacking factors such as light, bad weather, washing, permanent waving, perspiration and rubbing.

The dyeing method must also make it possible to cover white hairs and to obtain colourations and shades which are as unselective as possible, i.e. must make it possible to obtain the smallest possible colour differences along one and the same keratin fibre, which generally comprises areas that are differently sensitized (i.e. damaged) from its tip to its root.

The compositions used in the dyeing method must also have good mixing and application properties on keratin fibres, and in particular good rheological properties so as not to run, when they are applied, onto the face, onto the scalp or beyond the areas that it is proposed to dye.

Compositions in emulsion form must also be stable, especially in terms of "phase separation", i.e. not returning to two phases with the organic phase on one side and the aqueous phase on the other. Now, when a composition in direct emulsion form is oil-rich, i.e. comprising more than 25% by weight of oil relative to the total weight of the composition, instability of the emulsion often arises, in particular at high temperature.

Many attempts have been made in the field of lightening hair dyeing in order to improve the dyeing properties, for example using adjuvants. However, the choice of these adjuvants is difficult in so far as they must improve the dyeing properties of dyeing compositions without harming the other properties of these compositions. In particular, these adjuvants must not harm the keratin fibre-lightening properties when an oxidizing medium is employed and the colouration application properties.

European Patent Application EP 1 106 167 describes oxidation dyeing compositions comprising, besides dyes, a non-ionic compound derived from a long-chain ether of a polyoxyethylenated fatty alcohol. These compositions represented an improvement over the existing compositions, in particular in terms of viscosity and viscosity stability during the leave-on time on the hair.

A search is underway for ever more efficient colourations in terms of results, especially an improvement in the uptake of the colouration and better colour uniformity. A search is also underway for compositions with improved use qualities especially in terms of ease of distribution on the head of hair and of removal on rinsing.

The aim of the present invention is to obtain novel methods for the dyeing of keratin fibres which do not have the drawbacks of the prior art.

More particularly, the aim of the present invention is to make available a composition and a method for the dyeing of keratin fibres, exhibiting improved dyeing properties which make it possible, if appropriate, to achieve the desired lightening and which is easy to employ and apply, especially for which the mixture does not run but remains highly localized at the point of application. The term "improved dyeing properties" in particular means an improvement in the power/intensity and/or uniformity of the dyeing result.

These aims and others are achieved by the present invention, a subject-matter of which is thus a composition for dyeing keratin fibres, in particular human keratin fibres such as the hair, comprising:

i) at least one non-ionic ether of polyoxyalkylenated fatty alcohols, such as of formula (I):

$$R\text{—}(O\text{-Alk})_n\text{—}O\text{—}R' \qquad (I);$$

in which formula (I):
R denotes a saturated or unsaturated and linear or branched $C_{10}$-$C_{30}$ hydrocarbon radical,
R' denotes a saturated or unsaturated and linear or branched $C_{10}$-$C_{30}$ hydrocarbon radical which may be substituted, in particular by a hydroxyl radical,
n is an integer between 1 and approximately 100 inclusive, and
Alk represents a linear or branched, preferably linear, ($C_1$-$C_6$)alkylene group such as ethylene or propylene, preferably ethylene,
ii) at least one fatty substance,
iii) optionally at least one surfactant other than i),
iv) at least one direct dye and/or at least one oxidation dye,
v) optionally at least one basifying agent,
vi) optionally at least one chemical oxidizing agent, and
the fatty substance content of the composition representing in total at least 25% by weight relative to the total weight of the composition.

Another subject-matter of the invention is a dyeing method using the composition of the invention comprising or not comprising at least one chemical oxidizing agent, and a multicompartment device that enables the use of the composition of the invention.

Thus, the use of the dyeing composition according to the invention leads to powerful, intense, chromatic and/or sparingly selective colourations, i.e. colourations that are uniform along the fibre. The dyeing method of the invention also makes it possible to cover keratin fibres particularly well at their root, especially down to three centimeters from the base of said fibres. Moreover, the colours obtained after treating the fibres remain stable, in particular towards light.

The invention also makes it possible to reduce the amounts of active agents of the invention such as the direct dyes, oxidation dyes and/or oxidizing agents.

Furthermore, the methods according to the invention use formulations that are less malodorous during their application to the hair or during their preparation.

Other characteristics and advantages of the invention will emerge more clearly on reading the description and the examples that follow.

For the purposes of the present invention, and unless otherwise indicated:
the limits of a range of values are inclusive with regard to this range;
the human keratin fibres treated by the method according to the invention are preferably the hair.
the expression "inclusive" for a range of concentrations means that the limits of the range are included in the defined range.
the expression "at least one" followed by an ingredient is equivalent to the expression "one or more" ingredients.
the term "oxidizing agent" or "chemical oxidizing agent" according to the invention means an oxidizing agent other than atmospheric oxygen.
the term "direct emulsion" means a microscopically heterogeneous and macroscopically homogeneous mixture of two mutually immiscible liquid substances of oil-in-water (O/W) type. The emulsion is composed of an oily phase dispersed in an aqueous phase;
for the purposes of the present invention, the term "emulsion" thus means true emulsions, which are to be distinguished from microemulsions, which are thermodynamically stable systems, unlike true emulsions. The size of the droplets of the dispersed phase of the emulsions of the invention is preferably between 10 nm and 100 μm and preferably between 200 nm and 50 μm. This is the mean diameter D (3.2), which may be measured especially using a laser particle sizer. The direct emulsion may be prepared via standard emulsion preparation processes that are well known to those skilled in the art;
an "alkylene chain" represents a saturated and acyclic divalent $C_1$-$C_{20}$ hydrocarbon chain, in particular a $C_1$-$C_6$ hydrocarbon chain, more particularly a $C_1$-$C_2$ hydrocarbon chain when the chain is linear;
a "saturated or unsaturated divalent $C_{10}$-$C_{30}$ hydrocarbon chain" represents a hydrocarbon chain, in particular a $C_{10}$-$C_{20}$ hydrocarbon chain, optionally comprising one or more conjugated or non-conjugated double bonds; in particular, the hydrocarbon chain is saturated; said chain, when it is optionally substituted, is substituted by one or more identical or different groups chosen from i) hydroxyl, ii) ($C_1$-$C_2$)alkoxy, iii) (poly)hydroxy($C_2$-$C_4$)alcoxy(di)($C_1$-$C_2$) (alkyl)amino, iv) $R^a$—$Z^a$—C($Z^b$)—$Z^c$— and v) $R^a$—$Z^a$—S(O)$_t$—$Z^c$— with $Z^a$ and $Z^b$, which are identical or different, representing an oxygen or sulfur atom or an $NR^{a'}$ group, $Z^c$ representing a bond, an oxygen or sulfur atom or an $NR^a$ group, $R^a$ representing an alkali metal, a hydrogen atom or an alkyl group or else being absent if another part of the molecule is cationic, $R^{a'}$ representing a hydrogen atom or an alkyl group and t having the value 1 or 2; more particularly, the iv) groups are chosen from carboxylate —C(O)O⁻ or —C(O)OMetal (Metal=alkali metal), carboxyl —C(O)—OH, guanidino $H_2$N—C(NH)—NH—, amidino $H_2$N—C(NH)—, (thio)urea $H_2$N—C(O)—NH— and $H_2$N—C(S)—NH—, aminocarbonyl —C(O)—NRa'$_2$ or aminothiocarbonyl —C(S)—NRa'$_2$, or carbamoyl Ra'—C(O)—NRa'— or thiocarbamoyl Ra'—C(S)—NRa'— with Ra', which are identical or different, representing a hydrogen atom or a ($C_1$-$C_4$)alkyl group;
the "aryl" or "heteroaryl" radicals or the aryl or heteroaryl part of a radical may be substituted by at least one substituent carried by a carbon atom, chosen from:
a $C_1$-$C_{16}$ and preferably $C_1$-$C_8$ alkyl radical optionally substituted by one or more radicals chosen from hydroxyl, $C_1$-$C_2$ alkoxy, (poly)hydroxy($C_2$-$C_4$) alkoxy, acylamino or amino substituted by two $C_1$-$C_4$ alkyl radicals, which are identical or different, optionally carrying at least one hydroxyl group, or the two radicals possibly forming, with the nitrogen atom to which they are attached, a saturated or unsaturated and optionally substituted 5- to 7-membered and preferably 5- or 6-membered heterocycle optionally comprising another heteroatom identical to or different from nitrogen;
a halogen atom;
a hydroxyl group;
a $C_1$-$C_2$ alkoxy radical;
a (poly)hydroxy($C_2$-$C_4$)alkoxy radical;
an amino radical;
a 5- or 6-membered heterocycloalkyl radical;
an optionally cationic 5- or 6-membered heteroaryl radical, preferentially imidazolium, optionally substituted by a ($C_1$-$C_4$)alkyl radical, preferentially methyl;
an amino radical substituted by one or two identical or different $C_1$-$C_6$ alkyl radicals, optionally carrying at least:
i) a hydroxyl group,
ii) an amino group optionally substituted by one or two optionally substituted $C_1$-$C_3$ alkyl radicals, said alkyl radicals possibly forming, with the nitrogen atom to which they are attached, a saturated or unsaturated and optionally substituted 5- to 7-membered heterocycle, optionally comprising at least one other heteroatom identical to or different from nitrogen,
iii) a quaternary ammonium group —N⁺R'R"R"' M⁻ for which R', R" and R"', which are identical or different, represent a hydrogen atom or a $C_1$-$C_4$ alkyl group; and M⁻ represents the counterion of the corresponding organic acid, inorganic acid or halide;
iv) or an optionally cationic 5- or 6-membered heteroaryl radical, preferentially imidazolium, optionally substituted by a ($C_1$-$C_4$)alkyl radical, preferentially methyl;
an acylamino radical (—NR—C(O)R') in which the R radical is a hydrogen atom or a $C_1$-$C_4$ alkyl radical optionally carrying at least one hydroxyl group and the R' radical is a $C_1$-$C_2$ alkyl radical;
a carbamoyl radical ((R)$_2$N—C(O)—) in which the R radicals, which are identical or different, represent a hydrogen atom or a $C_1$-$C_4$ alkyl radical optionally carrying at least one hydroxyl group;
an alkylsulfonylamino radical (R'—S(O)$_2$—N(R)—) in which the R radical represents a hydrogen atom or a $C_1$-$C_4$ alkyl radical optionally carrying at least one hydroxyl group and the R' radical represents a $C_1$-$C_4$ alkyl radical or a phenyl radical;
an aminosulfonyl radical ((R)$_2$N—S(O)$_2$—) in which the R radicals, which are identical or different, represent a hydrogen atom or a $C_1$-$C_4$ alkyl radical optionally carrying at least one hydroxyl group;
a carboxylic radical in acid or salified form (preferably with an alkali metal or a substituted or unsubstituted ammonium);
a cyano group;
a nitro or nitroso group;
a polyhaloalkyl group, preferentially trifluoromethyl;
the cyclic or heterocyclic part of a non-aromatic radical may be substituted by at least one substituent chosen from the following groups:
hydroxyl;
$C_1$-$C_4$ alkoxy or (poly)hydroxy($C_2$-$C_4$)alkoxy;
($C_1$-$C_4$)alkyl;
alkylcarbonylamino (R—C(O)—N(R')—) in which the R' radical is a hydrogen atom or a $C_1$-$C_4$ alkyl radical optionally carrying at least one hydroxyl group and the R radical is a $C_1$-$C_2$ alkyl radical or an amino radical optionally substituted by one or two identical or different $C_1$-$C_4$ alkyl groups, themselves optionally carrying at least one hydroxyl group, said alkyl radicals possibly forming, with the nitrogen atom to which they are attached, a saturated or unsaturated and optionally substituted 5- to 7-membered heterocycle optionally comprising at least one other heteroatom identical to or different from nitrogen;
alkylcarbonyloxy (R—C(O)—O—) in which the R radical is a $C_1$-$C_4$ alkyl radical or an amino group optionally substituted by one or two identical or different $C_1$-$C_4$ alkyl groups, themselves optionally carrying at least one hydroxyl group, said alkyl radicals possibly forming, with the nitrogen atom to which they are attached, a saturated or unsaturated and optionally substituted 5- to 7-membered heterocycle optionally comprising at least one other heteroatom identical to or different from nitrogen;
alkoxycarbonyl (R-G-C(O)—) in which the R radical is a $C_1$-$C_4$ alkoxy radical and G is an oxygen atom or an amino group optionally substituted by a $C_1$-$C_4$ alkyl group itself optionally carrying at least one hydroxyl group, said alkyl radical possibly forming, with the nitrogen atom to which they are attached, a saturated or unsaturated and optionally substituted 5- to 7-membered heterocycle optionally comprising at least one other heteroatom identical to or different from nitrogen;
a cyclic or heterocyclic radical, or a non-aromatic part of an aryl or heteroaryl radical, may also be substituted with one or more oxo groups;
a hydrocarbon chain is unsaturated when it comprises one or more double bonds and/or one or more triple bonds;
an "aryl" radical represents a monocyclic or fused or non-fused polycyclic carbon-based group containing from 6 to 22 carbon atoms, at least one ring of which is aromatic; preferentially, the aryl radical is a phenyl, biphenyl, naphthyl, indenyl, anthracenyl or tetrahydronaphthyl;
a "heteroaryl radical" represents an optionally cationic, 5- to 22-membered, monocyclic or fused or non-fused polycyclic group, comprising from 1 to 6 heteroatoms chosen from nitrogen, oxygen, sulfur and selenium, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthyl and the ammonium salt thereof;
a "heterocyclic radical" is a 5- to 22-membered monocyclic or fused or non-fused polycyclic radical which can comprise one or two unsaturations but is non-aromatic, comprising from 1 to 6 heteroatoms chosen from nitrogen, oxygen, sulfur and selenium;
a "heterocycloalkyl radical" is a heterocyclic radical comprising at least one saturated ring;
a "cationic heteroaryl radical" is a heteroaryl group as defined previously, which comprises a quaternized endocyclic or exocyclic cationic group,
when the cationic charge is endocyclic, it is included in the electron delocalization via the mesomeric effect; for example, it is a pyridinium, imidazolium or indolinium group:

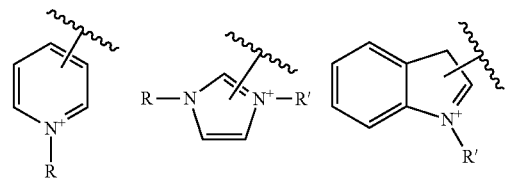

with R and R' being a heteroaryl substituent as defined previously and particularly a (hydroxy)($C_1$-$C_8$)alkyl group such as methyl;
when the cationic charge is exocyclic, for example, it is an ammonium or phosphonium R⁺ substituent, such as trimethylammonium, which is outside the heteroaryl, such as pyridinyl, indolyl, imidazolyl or naphthalimidyl, in question:

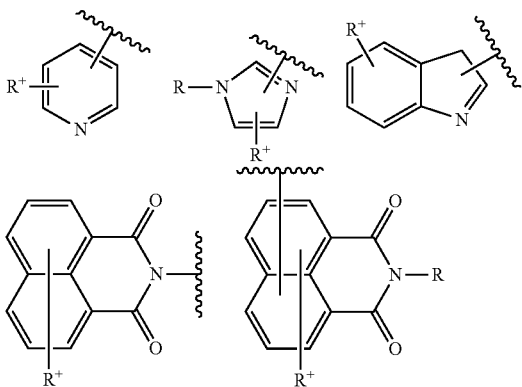

with R a heteroaryl substituent as defined previously and $R^+$ an ammonium $R_aR_bR_cN^+$—, phosphonium $R_aR_bR_cP^+$— or ammonium $R_aR_bR_cN^+$—$(C_1-C_6)$alkylamino group with $R_a$, $R_b$ and $R_c$, which are identical or different, representing a hydrogen atom or a $(C_1-C_8)$alkyl group, such as methyl;

the term "cationic aryl carrying an exocyclic charge" means an aryl ring whose quaternized cationic group is outside said ring; it is especially an ammonium or phosphonium $R^+$ substituent, such as trimethylammonium, which is outside the aryl, such as phenyl or naphthyl:

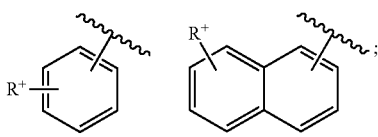

an "alkyl radical" is a linear or branched $C_1-C_{20}$ and preferably $C_1-C_8$ hydrocarbon radical;

an "alkylene radical" is a divalent hydrocarbon radical as defined previously which is saturated, the expression "optionally substituted" assigned to the alkyl or alkylene radical implies that said radicals can be substituted by one or more radicals chosen from i) hydroxyl radical, ii) $C_1-C_4$ alkoxy radical, iii) acylamino radical, iv) amino radical optionally substituted by one or two identical or different $C_1-C_4$ alkyl radicals, said alkyl radicals possibly forming, with the nitrogen atom which carries them, a 5- to 7-membered heterocycle optionally comprising another heteroatom identical to or different from nitrogen, v) a quaternary ammonium group —$N^+R'R''R'''$ $M^-$ for which R', R" and R"', which are identical or different, represent a hydrogen atom or a $C_1-C_4$ alkyl group, or else —$N^+R'R''R'''$ forms a heteroaryl, such as imidazolium, optionally substituted by a $C_1-C_4$ alkyl group, and $M^-$ represents the counterion of the corresponding organic acid, inorganic acid or halide, vi) $R^a$—$Z^a$—$C(Z^b)$—$Z^c$— and vii) $R^a$—$Z^a$—$S(O)_t$—$Z^c$— with $Z^a$ and $Z^b$, which are identical or different, representing an oxygen or sulfur atom or an $NR^{a'}$ group, $Z^c$ representing a bond, an oxygen or sulfur atom or an $NR^a$ group, $R^a$ representing an alkali metal, a hydrogen atom or an alkyl group or else being absent if another part of the molecule is cationic, $R^{a'}$ representing a hydrogen atom or an alkyl group and t having the value 1 or 2; more particularly, the substituents are chosen from carboxylate —C(O)O$^-$ or —C(O)OMetal (Metal=alkali metal), carboxyl —O(O)—OH, guanidino $H_2N$—C(NH)—NH—, amidino $H_2N$—C(NH)—, (thio)urea $H_2N$—C(O)—NH— and $H_2N$—C(S)—NH—, aminocarbonyl O(O)—$NR^{a'}_2$ or aminothiocarbonyl —C(S)—$NR^{a'}_2$, or carbamoyl $R^{a'}$—C(O)—$NR^{a'}$— or thiocarbamoyl $R^{a'}$—C(S)—$NR^{a'}$— with $R^{a'}$, which are identical or different, representing a hydrogen atom or a $(C_1-C_4)$alkyl group;

an "alkoxy radical" is an alkyl-oxy radical for which the alkyl radical is a linear or branched $C_1-C_{16}$, preferentially $C_1-C_8$, hydrocarbon radical; when the alkoxy group is optionally substituted, this implies that the alkyl group is optionally substituted as defined hereinabove;

an "organic or inorganic acid salt" more particularly means the salts chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)OH$; xiv) triflic acid $CF_3SO_3H$ and xv) tetrafluoroboric acid $HBF_4$;

an "anionic counterion" means an anion or an anionic group derived from an organic or inorganic acid salt which counterbalances the cationic charge of the dye; more particularly, the anionic counterion is chosen from: i) halides such as chloride or bromide; ii) nitrates; iii) sulfonates, including $C_1-C_6$ alkylsulfonates: Alk-S(O)$_2$O$^-$ such as methanesulfonate or mesylate, and ethanesulfonate; iv) arylsulfonates: Ar—S(O)$_2$O$^-$ such as benzenesulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$, O=P(O$^-$)$_2$—OH, O=P(O$^-$)$_3$ or HO—[P(O)(O$^-$)]$_w$—P(O)(O$^-$)$_2$ with w being an integer; xiv) acetate; xv) triflate; xvi) borates such as tetrafluoroborate, xvii) disulfate (O=)$_2$S(O$^-$)$_2$ or SO$_4^{2-}$ and monosulfate HSO$_4^-$;

the anionic counterion, derived from the organic or inorganic acid salt, ensures the electrical neutrality of the molecule; thus, it is understood that, when the anion comprises several anionic charges, then the same anion may serve for the electrical neutrality of several cationic groups in the same molecule or else may serve for the electrical neutrality of several molecules; for example, a disulfide dye of formula (I) which contains two cationic chromophores may contain either two "singly charged" anionic counterions or a "doubly charged" anionic counterion such as (O=)$_2$S(O$^-$)$_2$ or O=P(O$^-$)$_2$—OH;

moreover, the addition salts that may be used in the context of the invention are especially chosen from addition salts with a cosmetically acceptable base such as basifying agents as defined below, for instance alkali metal hydroxides, such as sodium hydroxide or potassium hydroxide, aqueous ammonia, amines or alkanolamines;

the expression "inclusive" for a range of concentrations means that the limits of the range are included in the defined range.

The human keratin fibres treated via the process according to the invention are preferably the hair.

The expression "at least one" followed by an ingredient is equivalent to the expression "one or more" ingredients.

The term "direct emulsion" means a microscopically heterogeneous and macroscopically homogeneous mixture of two mutually immiscible liquid substances of oil-in-water (O/W) type. The emulsion is composed of an oily phase dispersed in an aqueous phase.

For the purposes of the present invention, the term "emulsion" thus means true emulsions, which are to be distinguished from microemulsions, which are thermodynamically stable systems, unlike true emulsions. The size of the droplets of the dispersed phase of the emulsions of the invention is preferably between 10 nm and 100 μm and preferably between 200 nm and 50 μm. This is the mean diameter D (3.2), which may be measured especially using a laser particle sizer. The direct emulsion may be prepared via standard emulsion preparation processes that are well known to those skilled in the art.

The term "oxidizing agent" or "chemical oxidizing agent" according to the invention means an oxidizing agent other than atmospheric oxygen.

The Ingredients i) Non-Ionic Ether of Polyoxyalkylenated Fatty Alcohols

The composition according to the invention comprises at least one non-ionic ether of polyoxyalkylenated fatty alcohols.

The term "non-ionic ether of polyoxyalkylenated fatty alcohols" is understood to mean an ether derived or resulting from fatty alcohols, i.e. long-chain alcohols, preferably $C_8$-$C_{40}$ alcohols, which comprises one or more divalent $C_1$-$C_6$ alkoxyl groups: —[O-Alk]$_p$- with p an integer between 1 and 200 inclusive and Alk a $C_1$-$C_6$ alkylene group such as ethylene or propylene, preferably ethylene, one of the fatty chains of which can be substituted, preferably substituted by one or more hydroxyl groups, at least one hydroxyl group of which is in the β position relative to an ether functional group.

According to a specific embodiment of the invention, the non-ionic ether or ethers of polyoxyalkylenated fatty alcohols are chosen from the compounds of formula (I) below:

R—(O-Alk)$_n$-O—R'     (I), and also the optical isomers and geometrical isomers thereof; in which formula (I):

R denotes a saturated or unsaturated and linear or branched $C_{10}$-$C_{30}$ hydrocarbon radical, R' denotes a saturated or unsaturated and linear or branched $C_{10}$-$C_{30}$ hydrocarbon radical, which may be substituted by a hydroxyl radical, preferably substituted by the hydroxyl radical which occurs in the R position relative to the ether functional group, and n is an integer between 1 and approximately 100 inclusive, Alk represents a linear or branched, preferably linear, ($C_1$-$C_6$)alkylene group such as ethylene or propylene, preferably ethylene.

According to a particularly advantageous form of the invention, the Alk radical of the formula (I) represents a —CH$_2$—CH$_2$— group.

More particularly, the non-ionic ether of formula (I) is such that R and R', independently of each other, denote a saturated or unsaturated, preferably saturated, and linear or branched, preferably linear, $C_{12}$-$C_{20}$ and preferably $C_{14}$-$C_{18}$ hydrocarbon radical; R' possibly being substituted by at least one hydroxyl radical, and n denotes an integer greater than or equal to 20, for example ranging from 20 to 100 and preferably from 40 to 80.

Preferably, R and R' denote an alkyl radical.

According to a more preferred embodiment, the non-ionic ether of formula (I) is such that: R denotes a $C_{16}$-$C_{18}$ alkyl radical, which is preferably linear, and R' denotes a $C_{14}$ alkyl radical, which is preferably linear, substituted by an OH group, and n is equal to 60.

Preferably, the ether of formula (I) has the following formula

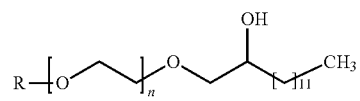

with R being a cetyl or stearyl group with n=60.

Such a compound is denoted, for example, in the CTFA dictionary under the name Ceteareth-60 myristyl glycol or Hydrogenated talloweth-60 myristyl glycol. A ceteareth-60 myristyl glycol is sold, for example, by the company Akzo under the trade name Elfacos GT 282 S.

In the composition according to the invention as defined previously, the non-ionic ether(s) of polyoxyalkylenated fatty alcohols are present in a concentration preferably ranging from 0.001% to 10%, more preferably still from 0.001% to 5% by weight, relative to the total weight of the composition of the invention.

ii) Fatty Substances

As has been mentioned, the composition of the invention comprises ii) one or more fatty substances.

The term "fatty substance" means an organic compound that is insoluble in water at ordinary temperature (25° C.) and at atmospheric pressure (760 mmHg) (solubility of less than 5%, preferably of less than 1% and more preferably still of less than 0.1%). They have in their structure at least one hydrocarbon chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Preferably, the fatty substances of the invention do not contain any salified or unsalified carboxylic acid groups (COOH or COO$^-$). Particularly, the fatty substances of the invention are neither polyoxyalkylenated nor polyglycerolated.

The term "oil" means a "fatty substance" that is liquid at ambient temperature (25° C.) and at atmospheric pressure (760 mmHg).

The term "non-silicone oil" means an oil not containing any silicon atoms (Si) and the term "silicone oil" means an oil containing at least one silicon atom.

More particularly, the fatty substances are chosen from $C_6$-$C_{16}$ alkanes, non-silicone oils of animal, vegetable, mineral or synthetic origin, fatty alcohols, esters of a fatty acid and/or of a fatty alcohol, non-silicone waxes and silicones.

It is recalled that, for the purpose of the invention, the fatty alcohols, esters and acids more particularly have at least one saturated or unsaturated and linear or branched hydrocarbon group comprising from 6 to 30 carbon atoms, which is optionally substituted, in particular by one or more hydroxyl groups (in particular 1 to 4). If they are unsaturated, these compounds may comprise one to three conjugated or unconjugated carbon-carbon double bonds.

As regards the $C_6$-$C_{16}$ alkanes, they are linear, branched or possibly cyclic. Examples that may be mentioned include hexane, dodecane and isoparaffins such as isohexadecane and isodecane.

As oils of animal, vegetable, mineral or synthetic origin that may be used in the composition of the invention, examples that may be mentioned include:

- hydrocarbon oils of animal origin, such as perhydrosqualene;
- triglyceride oils of vegetable or synthetic origin, such as liquid triglycerides of fatty acids containing from 6 to 30 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarinerie Dubois or those sold under the names Miglyol® 810, 812 and 818 by the company Dynamit Nobel, jojoba oil and shea butter oil;
- linear or branched hydrocarbons of mineral or synthetic origin, containing more than 16 carbon atoms, such as liquid paraffins, petroleum jelly, liquid petroleum jelly, polydecenes or hydrogenated polyisobutene such as Parleam®;
- fluoro oils, for instance perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-(trifluoromethyl)perfluoromorpholine sold under the name PF 5052® by the company 3M.

The fatty alcohols that are suitable for use in the invention are non-oxyalkylenated and non-glycerolated. They are particularly those of formula R—OH with R representing a linear or branched $C_8$-$C_{40}$ alkyl group or a linear or branched $C_8$-$C_{40}$ alkenyl group. More particularly, the fatty alcohols are unsaturated or branched alcohols, comprising from 8 to 30 carbon atoms.

Examples that may be mentioned include cetyl alcohol, stearyl alcohol and the mixture thereof, such as cetylstearyl alcohol, 2-octyldodecan-1-ol, 2-butyloctanol, 2-hexyldecanol, 2-undecylpentadecanol, oleyl alcohol and linoleyl alcohol. More particularly, the alcohols are $C_{20}$-$C_{22}$ alcohols.

As regards the esters of a fatty acid and/or of a fatty alcohol, which are advantageously different from the triglycerides mentioned above, mention may be made especially of esters of saturated or unsaturated and linear or branched $C_1$-$C_{26}$ aliphatic monoacids or polyacids and of saturated or unsaturated and linear or branched $C_1$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of monocarboxylic, dicarboxylic or tricarboxylic acids and of dihydroxy, trihydroxy, tetrahydroxy or pentahydroxy $C_2$-$C_{26}$ alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-comprising hydrocarbon compounds containing several alcohol functional groups, with or without aldehyde or ketone functional groups, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group consisting of the esters or mixtures of esters of sugars described previously and of saturated or unsaturated and linear or branched $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates or arachidonates, or mixtures thereof such as, especially, oleate/palmitate, oleate/stearate or palmitate/stearate mixed esters.

More particularly, use is made of monoesters and diesters and in particular mono- or di-oleate, -stearate, -behenate, -oleate/palmitate, -linoleate, -linolenate or -oleate/stearate of sucrose, glucose or methylglucose.

An example that may be mentioned is the product sold under the name Glucate® DO by the company Amerchol, which is a methylglucose dioleate.

Examples of esters or mixtures of esters of sugar and of fatty acid that may also be mentioned include:

- the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
- the products sold under the name Ryoto Sugar Esters, for example referenced B370 and corresponding to sucrose behenate formed from 20% monoester and 80% diester, triester and polyester;
- the sucrose monopalmitate/stearate-dipalmitate/stearate sold by the company Goldschmidt under the name Tegosoft® PSE.

The non-silicone wax(es) are chosen in particular from carnauba wax, candelilla wax, esparto wax, paraffin wax, ozokerite, vegetable waxes, such as olive tree wax, rice wax, hydrogenated jojoba wax or absolute flower waxes, such as the blackcurrant blossom essential wax sold by Bertin (France), or animal waxes, such as beeswaxes or modified beeswaxes (cerabellina); other waxes or waxy starting materials that can be used according to the invention are in particular marine waxes, such as that sold by Sophim under the reference M82, polyethylene waxes or polyolefin waxes in general.

The silicones that can be used in the cosmetic compositions of the present invention are volatile or non-volatile and cyclic, linear or branched silicones, which are unmodified or modified by organic groups, having a viscosity from $5 \times 10^{-6}$ to 2.5 $m^2/s$ at 25° C., and preferably from $1 \times 10^{-6}$ to 1 $m^2/s$.

The silicones that can be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from poly(oxyalkylene) groups, amino groups and alkoxy groups.

Organopolysiloxanes are defined in greater detail in Walter Noll's "Chemistry and Technology of Silicones" (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

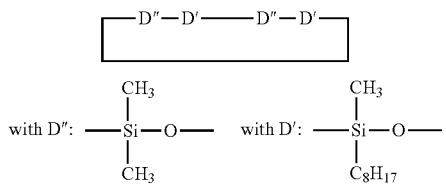

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ $m^2/s$ at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, "Volatile Silicone Fluids for Cosmetics".

Use is preferably made of non-volatile polydialkylsiloxanes, polydialkylsiloxane gums and resins, polyorganosiloxanes modified by the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:

- the Silbione® oils of the 47 and 70 047 series or the Mirasil® oils sold by Rhodia, for instance the oil 70 047 V 500 000;
- the oils of the Mirasil® series sold by the company Rhodia;
- the oils of the 200 series from the company Dow Corning, such as DC 200 with a viscosity of 60 000 $mm^2/s$;
- the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are polydi($C_1$-$C_{20}$)alkylsiloxanes.

The silicone gums that can be used in accordance with the invention are in particular polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane or tridecane, or mixtures thereof.

Products that can be used more particularly in accordance with the invention are mixtures such as:

- the mixtures formed from a hydroxy-terminated polydimethylsiloxane or dimethiconol (CTFA), and from a cyclic polydimethylsiloxane, also known as cyclomethicone (CTFA), such as the product Q2 1401 sold by the company Dow Corning;

mixtures of a polydimethylsiloxane gum and of a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities, and more particularly of a PDMS gum and a PDMS oil, such as the product SF 1236 from the company General Electric. The product SF 1236 is a mixture of a gum SE 30 defined above with a viscosity of 20 m²/s and of an oil SF 96 with a viscosity of $5 \times 10^{-6}$ m²/s. This product preferably comprises 15% of gum SE 30 and 85% of an oil SF 96.

The organopolysiloxane resins that can be used in accordance with the invention are crosslinked siloxane systems containing the following units:

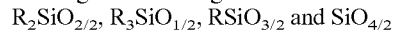

in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethylsiloxysilicate type resins sold in particular under the names X22-4914, X21-5034 and X21-5037 by the company Shin-Etsu.

The organomodified silicones that can be used in accordance with the invention are silicones as defined above and comprising in their structure one or more organofunctional groups attached via a hydrocarbon group.

Besides the silicones described above, the organomodified silicones may be polydiarylsiloxanes, in particular polydiphenylsiloxanes, and polyalkylarylsiloxanes functionalized by the organofunctional groups mentioned previously.

The polyalkylarylsiloxanes are chosen particularly from linear and/or branched polydimethyl/methylphenylsiloxanes and polydimethyl/diphenylsiloxanes with a viscosity of from $1 \times 10^{-5}$ to $5 \times 10^{-2}$ m²/s at 25° C.

Among these polyalkylarylsiloxanes, examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may be made of polyorganosiloxanes comprising:

polyethyleneoxy and/or polypropyleneoxy groups optionally comprising $C_6$-$C_{24}$ alkyl groups, such as the products named dimethicone copolyol sold by the company Dow Corning under the name DC 1248 or the oils Silwet® L 722, L 7500, L 77 and L 711 by the company Union Carbide, and the ($C_{12}$)alkyl methicone copolyol sold by the company Dow Corning under the name Q2 5200;

substituted or unsubstituted amino groups, such as the products sold under the name GP 4 Silicone Fluid and GP 7100 by the company Genesee, or the products sold under the names Q2 8220 and Dow Corning 929 or 939 by the company Dow Corning. The substituted amino groups are in particular $C_1$-$C_4$ aminoalkyl groups;

alkoxy groups such as the product sold under the name Silicone Copolymer F-755 by SWS Silicones, and Abil Wax® 2428, 2434 and 2440 by the company Goldschmidt.

Preferably, the fatty substances do not comprise any $C_2$-$C_3$ oxyalkylene units or any glycerol units.

More particularly, the fatty substances are chosen from compounds that are liquid or pasty at ambient temperature (25° C.) and at atmospheric pressure.

Preferably, the fatty substance is a compound that is liquid at a temperature of 25° C. and at atmospheric pressure.

The fatty substances are advantageously chosen from $C_6$-$C_{16}$ alkanes, non-silicone oils of vegetable, mineral or synthetic origin, fatty alcohols, esters of a fatty acid and/or of a fatty alcohol, and silicones, or mixtures thereof.

Preferably, the fatty substance is chosen from liquid petroleum jelly, $C_6$-$C_{16}$ alkanes, polydecenes, liquid esters of a fatty acid and/or of a fatty alcohol, and liquid fatty alcohols, or mixtures thereof.

Better still, the fatty substance is chosen from liquid petroleum jelly, $C_6$-$C_{16}$ alkanes and polydecenes.

The composition according to the invention comprises at least 30% by weight of fatty substances.

The composition according to the invention more particularly has a fatty substance content ranging from 25% to 80% by weight, preferably from 30% to 70% by weight, better still from 40% to 70% by weight and more advantageously still from 40% to 60% by weight relative to the weight of the composition.

iii) Surfactants

The composition of the invention can comprise iii) one or more surfactants different from the ether i) as defined previously.

In particular, the surfactant(s) are chosen from anionic, amphoteric, zwitterionic, cationic or non-ionic surfactants, and preferentially non-ionic surfactants.

The term "anionic surfactant" means a surfactant comprising, as ionic or ionizable groups, only anionic groups. These anionic groups are preferably chosen from the groups —C(O)OH, —C(O)O⁻, —SO₃H, —S(O)₂O⁻, —OS(O)₂OH, —OS(O)₂O⁻, —P(O)OH₂, —P(O)₂O⁻, —P(O)O₂⁻, —P(OH)₂, =P(O)OH, —P(OH)O⁻, =P(O)O⁻, =POH, =PO⁻, the anionic parts comprising a cationic counterion such as an alkali metal, an alkaline earth metal or an ammonium.

Mention may be made, as examples of anionic surfactants that can be used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyl taurates, salts of alkyl monoesters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids; and the corresponding non-salified forms of all these compounds, the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids can be selected from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, it (they) may be chosen from alkali metal salts such as the sodium or potassium salt and preferably the sodium salt, ammonium salts, amine salts and in particular aminoalcohol salts, or alkaline earth metal salts such as the magnesium salts.

Examples of aminoalcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline earth metal salts, and in particular sodium or magnesium salts.

Among the anionic surfactants mentioned, use is preferably made of ($C_6$-$C_{24}$)alkyl sulfates, ($C_6$-$C_{24}$)alkyl ether sulfates comprising from 2 to 50 ethylene oxide units, especially in the form of alkali metal, ammonium, aminoalcohol and alkaline earth metal salts, or a mixture of these compounds.

In particular, it is preferred to use ($C_{12}$-$C_{20}$)alkyl sulfates, ($C_{12}$-$C_{20}$)alkyl ether sulfates comprising from 2 to 20 ethylene oxide units, especially in the form of alkali metal, ammonium, aminoalcohol and alkaline earth metal salts, or a mixture of these compounds. Better still, it is preferred to use sodium lauryl ether sulfate containing 2.2 mol of ethylene oxide.

The amphoteric or zwitterionic surfactant(s), which is (are) preferably non-silicone surfactant(s), which can be used in the present invention may especially be derivatives of optionally quaternized secondary or tertiary aliphatic amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group. Mention may be made in particular of ($C_8$-$C_{20}$)alkyl betaines, sulfobetaines, ($C_8$-$C_{20}$)alkylamido($C_3$-$C_8$)alkyl betaines and ($C_8$-$C_{20}$)alkylamido($C_6$-$C_8$)alkyl sulfobetaines.

Among the optionally quaternized secondary or tertiary aliphatic amine derivatives that can be used, as defined above, mention may also be made of the compounds of respective structures (A1) and (A2) below:

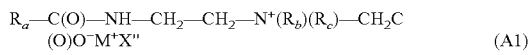

(A1)

in which formula (A1):
$R_a$ represents a $C_{10}$-$C_{30}$ alkyl or alkenyl group derived from an acid $R_a$COOH preferably present in hydrolysed coconut oil, or a heptyl, nonyl or undecyl group;
$R_b$ represents a β-hydroxyethyl group; and
$R_c$ represents a carboxymethyl group;
$M^+$ represents a cationic counterion derived from an alkali metal or alkaline earth metal, such as sodium, an ammonium ion or an ion derived from an organic amine, and
$X^-$ represents an organic or inorganic anionic counterion, such as that chosen from halides, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate; or alternatively $M^+$ and $X^-$ are absent;

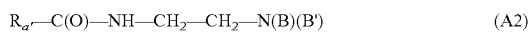

(A2)

in which formula (A2):
B represents the group —$CH_2$—$CH_2$—O—X';
B' represents the group —$(CH_2)_zY'$, with z=1 or 2;
X' represents the group —$CH_2$—C(O)OH, —$CH_2$—C(O)OZ', —$CH_2$—$CH_2$—C(O)OH or —$CH_2$—$CH_2$—C(O)OZ', or a hydrogen atom;
Y' represents the group —C(O)OH, —C(O)OZ' or —$CH_2$—CH(OH)—$SO_3$H or the group —$CH_2$—CH(OH)—$SO_3$—Z';
Z' represents a cationic counterion derived from an alkali metal or alkaline earth metal, such as sodium, an ammonium ion or an ion derived from an organic amine;
$R_{a'}$ represents a $C_{10}$-$C_{30}$ alkyl or alkenyl group of an acid $R_a$—C(O)OH preferably present in hydrolysed linseed oil or coconut oil, an alkyl group, especially a $C_{17}$ alkyl group, and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Among the amphoteric or zwitterionic surfactants mentioned above, use is preferably made of ($C_8$-$C_{20}$)alkyl betaines such as coco betaine, and ($C_8$-$C_{20}$)alkylamido($C_3$-$C_8$)alkyl betaines such as cocamidopropyl betaine, and mixtures thereof. More preferentially, the amphoteric or zwitterionic surfactant(s) are chosen from cocamidopropyl betaine and coco betaine.

The cationic surfactant(s) that can be used in the composition according to the invention comprise, for example, salts of optionally polyoxyalkylenated primary, secondary or tertiary fatty amines, quaternary ammonium salts, and mixtures thereof.

Examples of quaternary ammonium salts that may especially be mentioned include:
those corresponding to the general formula (A3) below:

(A3)

in which formula (A3):
$R_8$ to $R_{11}$, which are identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and
$X^-$ represents an organic or inorganic anionic counterion, such as that chosen from halides, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate.

The aliphatic groups of $R_8$ to $R_{11}$ may also comprise heteroatoms, especially such as oxygen, nitrogen, sulfur and halogens.

The aliphatic groups of $R_5$ to $R_{11}$ are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-

$C_{22}$)alkyl acetate and hydroxy($C_1$-$C_{30}$)alkyl groups, and $X^-$ is an anionic counterion chosen from halides, phosphates, acetates, lactates, ($C_1$-$C_4$)alkyl sulfates, or ($C_1$-$C_4$)alkyl- or ($C_1$-$C_4$)alkylarylsulfonates.

Among the quaternary ammonium salts of formula (A3), preference is given firstly to tetraalkylammonium chlorides, for instance dialkyldimethylammonium or alkyltrimethylammonium chlorides in which the alkyl group contains approximately from to 22 carbon atoms, in particular behenyltrimethylammonium chloride, distearyldimethylammonium chloride, cetyltrimethylammonium chloride or benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (A4) below:

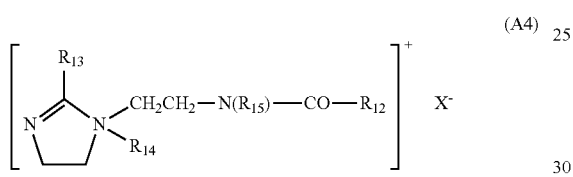

(A4)

in which formula (A4):
- $R_{12}$ represents an alkenyl or alkyl group comprising from 8 to 30 carbon atoms, for example tallow fatty acid derivatives;
- $R_{13}$ represents a hydrogen atom, a $C_1$-$C_4$ alkyl group or an alkenyl or alkyl group comprising from 8 to 30 carbon atoms;
- $R_{14}$ represents a $C_1$-$C_4$ alkyl group;
- $R_{15}$ represents a hydrogen atom or a $C_1$-$C_4$ alkyl group;
- $X^-$ represents an organic or inorganic anionic counterion, such as that chosen from halides, phosphates, acetates, lactates, ($C_1$-$C_4$)alkyl sulfates, or ($C_1$-$C_4$)alkyl- or ($C_1$-$C_4$)alkylarylsulfonates.

$R_{12}$ and $R_{13}$ preferably denote a mixture of alkenyl or alkyl groups comprising from 12 to 21 carbon atoms, for example tallow fatty acid derivatives, $R_{14}$ denotes a methyl group and $R_{15}$ denotes a hydrogen atom. Such a product is sold, for example, under the name Rewoquat® W 75 by the company Rewo;

di- or triquaternary ammonium salts, in particular of formula (A5) below:

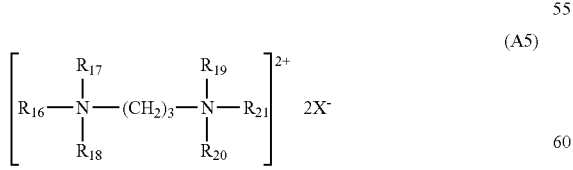

(A5)

in which formula (A5):
- $R_{16}$ denotes an alkyl group comprising approximately from 16 to 30 carbon atoms, which is optionally hydroxylated and/or interrupted by one or more oxygen atoms;
- $R_{17}$ is chosen from hydrogen, an alkyl group comprising from 1 to 4 carbon atoms or a $-(CH_2)_3-N^+(R_{16a})(R_{17a})(R_{18a})X^-$ group;
- $R_{16a}$, $R_{17a}$, $R_{18a}$, $R_{18}$, $R_{19}$, $R_{20}$ and $R_{21}$, which are identical or different, are chosen from hydrogen and an alkyl group comprising from 1 to 4 carbon atoms; and
- $X^-$, which are identical or different, represents an organic or inorganic anionic counterion, such as that chosen from halides, acetates, phosphates, nitrates, ($C_1$-$C_4$)alkyl sulfates, or ($C_1$-$C_4$)alkyl- or ($C_1$-$C_4$)alkylarylsulfonates, in particular methyl sulfate and ethyl sulfate.

Such compounds are, for example, Finquat CT-P, provided by the company Finetex (Quaternium 89), and Finquat CT, provided by the company Finetex (Quaternium 75);

quaternary ammonium salts containing one or more ester functional groups, such as those of formula (A6) below:

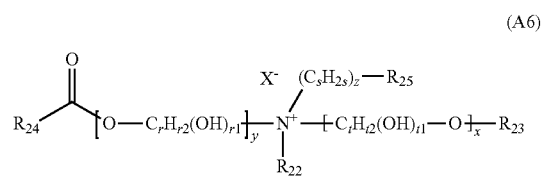

(A6)

in which formula (A6):
- $R_{22}$ is chosen from $C_1$-$C_6$ alkyl and $C_1$-$C_6$ hydroxyalkyl or dihydroxyalkyl groups,
- $R_{23}$ is chosen from:
  the group

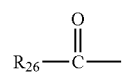

saturated or unsaturated and linear or branched $C_1$-$C_{22}$ hydrocarbon groups $R_{27}$,
  a hydrogen atom,
- $R_{25}$ is chosen from:
  the group

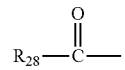

saturated or unsaturated and linear or branched $C_1$-$C_6$ hydrocarbon groups $R_{29}$,
  a hydrogen atom,
- $R_{24}$, $R_{26}$ and $R_{28}$, which are identical or different, are chosen from saturated or unsaturated and linear or branched $C_7$-$C_{21}$ hydrocarbon groups;
- r, s and t, which are identical or different, are integers having values from 2 to 6,
- r1 and t1, which are identical or different, have the value 0 or 1, with r2+r1=2r and t1+t2=2t,
- y is an integer having a value from 1 to 10,
- x and z, which are identical or different, are integers having values from 0 to 10,
- $X^-$ represents an organic or inorganic anionic counterion, with the proviso that the sum x+y+z has a value from 1 to 15, that, when x has the value 0, then $R_{23}$ denotes $R_{27}$ and that, when z has the value 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z has a value from 1 to 10.

When $R_{23}$ is a hydrocarbon group $R_{27}$, it may be long and contain from 12 to 22 carbon atoms, or may be short and contain from 1 to 3 carbon atoms.

When $R_{25}$ is a hydrocarbon group $R_{29}$, it preferably contains 1 to 3 carbon atoms.

Advantageously, $R_{24}$, $R_{26}$ and $R_{28}$, which are identical or different, are chosen from saturated or unsaturated and linear or branched $C_{11}$-$C_{21}$ hydrocarbon groups, and more particularly from saturated or unsaturated and linear or branched $C_{11}$-$C_{21}$ alkyl and alkenyl groups.

Preferably, x and z, which are identical or different, have the value 0 or 1.

Advantageously, y is equal to 1.

Preferably, r, s and t, which are identical or different, have the value 2 or 3, and even more particularly are equal to 2.

The anionic counterion $X^-$ is preferably a halide, such as chloride, bromide or iodide; a $(C_1$-$C_4)$alkyl sulfate; or a $(C_1$-$C_4)$alkyl- or $(C_1$-$C_4)$alkylarylsulfonate. However, it is possible to use methanesulfonate, phosphate, nitrate, tosylate, an anion derived from an organic acid, such as acetate or lactate, or any other anion that is compatible with the ammonium containing an ester functional group.

The anionic counterion $X^-$ is even more particularly chloride, methyl sulfate or ethyl sulfate.

Use is made more particularly in the composition according to the invention of the ammonium salts of formula (A6) in which:
$R_{22}$ denotes a methyl or ethyl group,
x and y are equal to 1,
z is equal to 0 or 1,
r, s and t are equal to 2,
$R_{23}$ is chosen from:
  the group

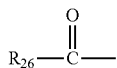

methyl, ethyl or $C_{14}$-$C_{22}$ hydrocarbon groups,
  a hydrogen atom,
$R_{25}$ is chosen from:
  the group

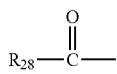

a hydrogen atom,
$R_{24}$, $R_{26}$ and $R_{28}$, which are identical or different, are chosen from saturated or unsaturated and linear or branched $C_{13}$-$C_{17}$ hydrocarbon groups, and preferably from saturated or unsaturated and linear or branched $C_{13}$-$C_{17}$ alkyl and alkenyl groups.

Advantageously, the hydrocarbon radicals are linear.

Among the compounds of formula (A6), examples that may be mentioned include salts, especially the chloride or methyl sulfate, of diacyloxyethyldimethylammonium, diacyloxyethylhydroxyethylmethylammonium, monoacyloxyethyldihydroxyethylmethyl-ammonium, triacyloxyethylmethylammonium or monoacyloxyethylhydroxyethyldimethylammonium, and mixtures thereof. The acyl groups preferably contain 14 to 18 carbon atoms and are obtained more particularly from a vegetable oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of vegetable or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

It is also possible to use the ammonium salts containing at least one ester functional group that are described in U.S. Pat. No. 4,874,554 and U.S. Pat. No. 4,137,180.

Use may be made of behenoylhydroxypropyltrimethylammonium chloride, provided by Kao under the name Quatarmin BTC 131.

Preferably, the ammonium salts containing at least one ester functional group contain two ester functional groups.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride and dipalmitoylethylhydroxyethylammonium methosulfate, and mixtures thereof.

Examples of non-ionic surfactants that can be used in the composition used according to the invention are described, for example, in the "Handbook of Surfactants" by M. R. Porter, published by Blackie & Son (Glasgow and London), 1991, pp. 116-178. They are especially chosen from alcohols, α-diols and $(C_1$-$C_{20})$alkylphenols, these compounds being polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50 and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, optionally oxyalkylenated alkyl polyglycosides, alkyl glucoside esters, derivatives of N-alkylglucamine and of N-acylmethylglucamine, aldobionamides and amine oxides.

The non-ionic surfactants are more particularly chosen from mono-oxyalkylenated or polyoxyalkylenated and monoglycerolated or polyglycerolated non-ionic surfactants.

The oxyalkylene units are more particularly oxyethylene or oxypropylene units, or a combination thereof, preferably oxyethylene units.

Examples of oxyalkylenated non-ionic surfactants that may be mentioned include:
oxyalkylenated ($C_8$-$C_{24}$)alkylphenols;
saturated or unsaturated and linear or branched oxyalkylenated $C_8$-$C_{30}$ alcohols;
saturated or unsaturated and linear or branched oxyalkylenated $C_8$-$C_{30}$ amides;
esters of saturated or unsaturated and linear or branched $C_8$-$C_{30}$ acids and of polyethylene glycols;
polyoxyethylenated esters of saturated or unsaturated and linear or branched $C_8$-$C_{30}$ acids and of sorbitol;
saturated or unsaturated oxyethylenated vegetable oils;
condensates of ethylene oxide and/or of propylene oxide, inter alia, alone or as mixtures;
oxyethylenated and/or oxypropylenated silicones.

The surfactants contain a number of moles of ethylene oxide and/or of propylene oxide of between 1 and 100, preferably between 2 and 50 and preferably between 2 and 30. Advantageously, the non-ionic surfactants do not comprise any oxypropylene units.

In accordance with a preferred embodiment of the invention, the oxyalkylenated non-ionic surfactants are chosen from oxyethylenated $C_9$-$C_{30}$ alcohols comprising from 1 to 100 mol of ethylene oxide; and polyoxyethylenated esters of saturated or unsaturated and linear or branched $C_9$-$C_{30}$ acids and of sorbitol comprising from 1 to 100 mol of ethylene oxide.

As examples of monoglycerolated or polyglycerolated non-ionic surfactants, monoglycerolated or polyglycerolated $C_9$-$C_{40}$ alcohols are preferably used.

In particular, the monoglycerolated or polyglycerolated $C_9$-$C_{40}$ alcohols correspond to the formulae (A7) and (A'7) below:

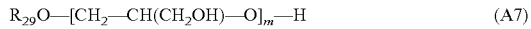

$$R_{29}O—[CH_2—CH(CH_2OH)—O]_m—H \qquad (A7)$$

$$H—[OCH_2—CH(CH_2OH)]_m—OR_{29} \qquad (A'7)$$

in which formulae (A7) and (A'7):
$R_{29}$ represents a linear or branched $C_9$-$C_{40}$ and preferably $C_9$-$C_{30}$ alkyl or alkenyl radical; and
m represents a number ranging from 1 to 30 and preferably from 1 to 10.

As examples of compounds of formula (A7) or (A'7) that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleyl/cetyl alcohol containing 6 mol of glycerol, and octadecanol containing 6 mol of glycerol.

The alcohol of formula (A7) or (A'7) may represent a mixture of alcohols in the same way as the value of m represents a statistical value, which means that, in a commercial product, several types of polyglycerolated fatty alcohols may coexist in the form of a mixture.

Among the monoglycerolated or polyglycerolated alcohols, it is more particularly preferred to use the $C_8$-$C_{10}$ alcohol containing 1 mol of glycerol, the $C_{10}$-$C_{12}$ alcohol containing 1 mol of glycerol and the $C_{12}$ alcohol containing 1.5 mol of glycerol.

Preferably, the surfactant(s) are chosen from non-ionic surfactants other than the non-ionic ethers of polyoxyalkylenated fatty alcohols of formula i) or from anionic surfactants. More particularly, the surfactant(s) present in the composition are chosen from non-ionic surfactants.

Preferably, the surfactant(s) used in the process of the invention or in the composition are mono- or polyoxyalkylenated, particularly mono- or polyoxyethylenated or mono- or polyoxypropylenated, non-ionic surfactants, or a combination thereof, more particularly mono- or polyoxyethylenated non-ionic surfactants.

Even more preferentially, the non-ionic surfactants are chosen from polyoxyethylenated esters of sorbitol, oxyethylenated $C_8$-$C_{30}$ alcohols comprising from 1 to 100, preferably between 2 and 50 and even more particularly between 2 and 30 mol of ethylene oxide, other than the non-ionic ethers of polyoxyalkylenated fatty alcohols of formula (i), and mixtures thereof. Even more preferentially, the non-ionic surfactants are chosen from the abovementioned oxyethylenated $C_8$-$C_{30}$ alcohols.

In the composition of the invention, the amount of surfactant(s) in the composition preferably varies from 0.1% to 50% by weight and better still from 0.5% to 20% by weight relative to the total weight of the composition.

iv) Direct Dyes and Oxidation Dyes:

The composition of the invention comprises a) one or more direct dyes and/or one or more oxidation dyes which will be described in detail below.

The term "direct dye" means natural and/or synthetic dyes, other than oxidation dyes. These are dyes that will spread superficially on the fibre.

They can be ionic or non-ionic, preferably cationic or non-ionic, either as sole dyes.

These direct dyes are chosen, for example, from neutral, acidic or cationic nitrobenzene direct dyes, neutral, acidic or cationic azo direct dyes, tetraazapentamethine dyes, neutral, acidic or cationic quinone and in particular anthraquinone dyes, azine direct dyes, triarylmethane direct dyes, azomethine direct dyes and natural direct dyes.

Examples of suitable direct dyes that may be mentioned include azo direct dyes; (poly)methine dyes such as cyanines, hemicyanines and styryl dyes; carbonyl dyes; azine dyes; nitro(hetero)aryl dyes; tri(hetero)arylmethane dyes; porphyrin dyes; phthalocyanine dyes, and natural direct dyes, alone or as mixtures.

Preferentially, the direct dye(s) contain(s) at least one quaternized cationic chromophore or at least one chromophore carrying a quaternized or quaternizable cationic group.

According to a specific embodiment of the invention, the direct dyes comprise at least one quaternized cationic chromophore.

As direct dye according to the invention, mention may be made of the following dyes: acridines; acridones; anthranthrones; anthrapyrimidines; anthraquinones; azines; (poly) azos, hydrazonos or hydrazones, in particular arylhydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanines such as azacarbocyanines, diazacarbocyanines, diazahemicyanines, hemicyanines or tetraazacarbocyanines; diazines; diketopyrrolopyrroles; dioxazines; diphenylamines; diphenylmethanes; dithiazines; flavonoids such as flavanthrones and flavones; fluorindines; formazans; indamines; indanthrones; indigoids and pseudo-indigoids; indophenols; indoanilines; isoindolines; isoindolinones; isoviolanthrones; lactones; (poly)methines such as dimethines of stilbene or styryl type; naphthalimides; naphthanilides; naphtholactams; naphthoquinones; nitro, especially nitro(hetero)aromatics; oxadiazoles; oxazines; perilones; perinones; perylenes; phenazines; phenoxazine; phenothiazines; phthalocyanine; polyenes/carotenoids; porphyrins; pyranthrones; pyrazolanthrones; pyrazolones; pyrimidinoanthrones; pyronines; quinacridones; quinolines; quinophthalones; squaranes; tetrazoliums; thiazines; thioindigo; thiopyronines; triarylmethanes or xanthenes.

Among the cationic azo dyes, mention may be made particularly of those derived from the cationic dyes described in the Kirk-Othmer Encyclopedia of Chemical Technology, "Dyes, Azo", J. Wiley & Sons, updated on Apr. 19, 2010.

Mention may be made, among the azo dyes which can be used according to the invention, of the cationic azo dyes described in Patent Applications WO 95/15144, WO 95/01772 and EP-714 954.

According to a preferred embodiment of the invention, the direct dye(s) are chosen from cationic dyes known as "basic dyes".

Among the azo dyes, mention may be made of those described in the Colour Index International 3rd edition, and especially the following compounds:
Basic Red 22
Basic Red 76
Basic Yellow 57
Basic Brown 16
Basic Brown 17

Among the cationic quinone dyes, those mentioned in the abovementioned Colour Index International are suitable and, among these, mention may be made, inter alia, of the following dyes:
Basic Blue 22
Basic Blue 99

Among the azine dyes which are suitable, mention may be made of those listed in the Colour Index International and for example the following dyes:
Basic Blue 17
Basic Red 2.

Among the cationic triarylmethane dyes that may be used according to the invention, mention may be made, besides those listed in the Colour Index, of the following dyes:
Basic Green 1
Basic Violet 3
Basic Violet 14
Basic Blue 7
Basic Blue 26.

Mention may also be made of the cationic dyes described in the documents U.S. Pat. No. 5,888,252, EP 1 133 975, WO 03/029 359, EP 850 636, WO 95/01772, WO 95/15144 and EP 714 954. Mention may also be made of those listed in the encyclopaedia "The Chemistry of Synthetic Dyes" by K. Venkataraman, 1952, Academic Press, vol. 1 to 7, in the "Kirk-Othmer Encyclopedia of Chemical Technology", in the chapter "Dyes and Dye Intermediates", 1993, Wiley and Sons, and in various chapters of "Ullmann's Encyclopedia of Industrial Chemistry", 7th edition, Wiley and Sons.

Preferably, the cationic direct dyes are chosen from those derived from dyes of azo and hydrazono type.

According to a particular embodiment, the direct dyes are cationic azo dyes described in EP 850 636, FR 2 788 433, EP 920 856, WO 99/48465, FR 2 757 385, EP 85/0637, EP 91/8053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 01/66646, U.S. Pat. No. 5,708,151, WO 95/01772, WO 515 144, GB 1 195 386, U.S. Pat. No. 3,524,842, U.S. Pat. No. 5,879,413, EP 1 062 940, EP 1 133 976, GB 738 585, DE 2 527 638, FR 2 275 462, GB 1974-27645, *Acta Histochem.* (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

Preferably, the cationic direct dye(s) comprise(s) a quaternary ammonium group; more preferentially, the cationic charge is endocyclic.

These cationic radicals are, for example, a cationic radical:
carrying an exocyclic (di/tri)($C_1$-$C_8$)alkylammonium charge, or
carrying an endocyclic charge such as comprising a cationic heteroaryl group chosen from: acridinium, benzimidazolium, benzobistriazolium, benzopyrazolium, benzopyridazinium, benzoquinolium, benzothiazolium, benzotriazolium, benzoxazolium, bipyridinium, bis-tetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, phenazinium, phenoxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

Mention may be made of the hydrazono cationic dyes of formulae (II) and (III), and the azo cationic dyes of formulae (IV) and (V) below:

(II)

(III)

(IV)

(V)

in which formulae (II) to (V):
Het$^+$ represents a cationic heteroaryl radical, preferentially carrying an endocyclic cationic charge, such as imidazolium, indolium or pyridinium, which is optionally substituted, preferentially by at least one ($C_1$-$C_8$)alkyl group such as methyl;
Ar$^+$ represents an aryl radical, such as phenyl or naphthyl, carrying an exocyclic cationic charge, preferentially ammonium, particularly tri($C_1$-$C_8$)alkylammonium such as trimethylammonium;
Ar represents an aryl group, especially phenyl, which is optionally substituted, preferentially by one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) by a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar″ represents an optionally substituted (hetero)aryl group such as phenyl or pyrazolyl, which are optionally substituted, preferentially by one or more $(C_1-C_8)$alkyl, hydroxyl, (di)$(C_1-C_8)$(alkyl)amino, $(C_1-C_8)$alkoxy or phenyl groups;

$R_a$ and $R_b$, which are identical or different, represent a hydrogen atom or a $(C_1-C_8)$alkyl group, which is optionally substituted, preferentially by a hydroxyl group;

or else the substituent $R_a$ with a substituent of $Het^+$ and/or $R_b$ with a substituent of Ar form, together with the atoms which carry them, a (hetero)cycloalkyl; in particular, $R_a$ and $R_b$ represent a hydrogen atom or a $(C_1-C_4)$alkyl group optionally substituted by a hydroxyl group;

$Q^-$ represents an organic or inorganic anionic counterion such as a halide or an alkyl sulfate;

In particular, mention may be made of the azo and hydrazono direct dyes carrying an endocyclic cationic charge of formulae (II) to (V) as defined previously, more particularly the cationic direct dyes of formulae (II) to (V) carrying an endocyclic cationic charge described in Patent Applications WO 95/15144, WO 95/01772 and EP-714 954, preferentially the following direct dyes:

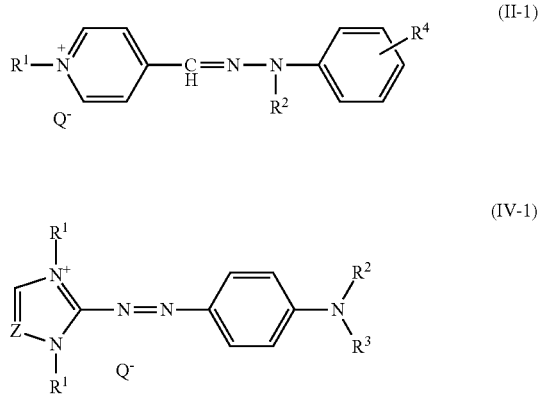

in which formulae (II-1) and (IV-1):

$R^1$ represents a $(C_1-C_4)$alkyl group such as methyl;

$R^2$ and $R^3$, which are identical or different, represent a hydrogen atom or a $(C_1-C_4)$alkyl group such as methyl; and $R^4$ represents a hydrogen atom or an electron-donating group such as optionally substituted $(C_1-C_8)$alkyl, optionally substituted $(C_1-C_8)$alkoxy, or (di)$(C_1-C_8)$(alkyl)amino optionally substituted on the alkyl group(s) by a hydroxyl group; particularly, $R^4$ is a hydrogen atom, Z represents a CH group or a nitrogen atom, preferentially CH, $Q^-$ is an anionic counterion as defined previously, particularly a halide such as chloride or an alkyl sulfate such as methyl sulfate or mesityl.

Particularly, the dyes of formulae (II-1) and (IV-1) are chosen from Basic Red 51, Basic Yellow 87 and Basic Orange 31 or derivatives thereof:

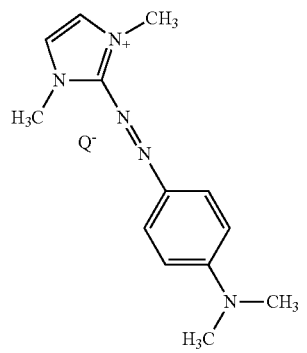

Basic Red 51

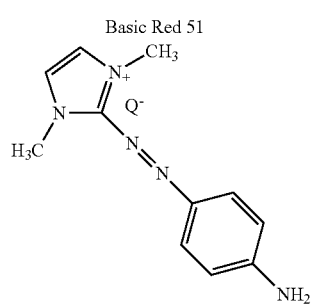

Basic Orange 31

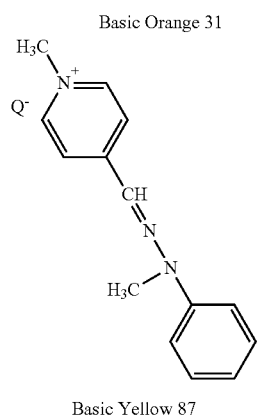

Basic Yellow 87 with Q' an anionic counterion as defined previously, particularly a halide such as chloride or an alkyl sulfate such as methyl sulfate or mesityl.

According to a particular embodiment of the invention, the direct dyes are fluorescent, i.e. they contain at least one fluorescent chromophore as defined previously.

As fluorescent dyes, mention may be made of radicals derived from the following dyes: acridines, acridones, benzanthrones, benzimidazoles, benzimidazolones, benzindoles, benzoxazoles, benzopyrans, benzothiazoles, coumarins, difluoro{2-[(2H-pyrrol-2-ylidene-kN)methyl]-1H-pyrrolato-kN}borons (BODIPY®), diketopyrrolopyrroles, fluorindines, (poly)methines (especially cyanines and styryls/hemicyanines), naphthalimides, naphthanilides, naphthylamine (such as dansyls), oxadiazoles, oxazines, perilones, perinones, perylenes, polyenes/carotenoids, squaranes, stilbenes and xanthenes.

Mention may also be made of the fluorescent dyes described in the documents EP 1 133 975, WO 03/029 359, EP-850 636, WO 95/01772, WO 95/15144 and EP 714 954 and those listed in the encyclopaedia "The Chemistry of Synthetic Dyes" by K. Venkataraman, 1952, Academic Press, vol. 1 to 7, in the "Kirk-Othmer Encyclopedia of Chemical Technology", in the chapter "Dyes and Dye Intermediates", 1993, Wiley and Sons, and in various chapters of "Ullmann's Encyclopedia of Industrial Chemistry", 7$^{th}$ edition, Wiley and Sons, and in the handbook—"A Guide to Fluorescent Probes and Labeling Technologies", 10th Ed., Molecular Probes/Invitrogen—Oregon 2005, circulated on the Internet or in the preceding printed editions.

According to a preferred alternative form of the invention, the fluorescent dye(s) are cationic and comprise at least one quaternary ammonium radical, such as those of following formula (V):

$$W^+-[C(R_c)=C(R_d)]_{m'}-Ar'Q^-  \quad (V)$$

in which formula (V):
- $W^+$ represents a cationic heterocyclic or heteroaryl group, particularly comprising a quaternary ammonium optionally substituted by one or more $(C_1-C_8)$alkyl groups, optionally substituted especially by one or more hydroxyl groups;
- Ar represents an aryl group such as phenyl or naphthyl, optionally substituted preferentially by i) one or more halogen atoms such as chlorine or fluorine; ii) one or more $(C_1-C_8)$alkyl groups, preferably of $C_1-C_4$ such as methyl; iii) one or more hydroxyl groups; iv) one or more $(C_1-C_8)$alkoxy groups such as methoxy; v) one or more hydroxy$(C_1-C_8)$alkyl groups such as hydroxyethyl, vi) one or more amino or (di)$(C_1-C_8)$alkylamino groups, preferably with the $C_1-C_4$ alkyl part optionally substituted by one or more hydroxyl groups, such as (di)hydroxyethylamino, vii) one or more acylamino groups; viii) one or more heterocycloalkyl groups such as piperazinyl, piperidyl or 5- or 6-membered heteroaryl such as pyrrolidinyl, pyridyl and imidazolinyl;
- m' represents an integer between 1 and 4 inclusive, and in particular m has the value 1 or 2; more preferentially 1;
- $R_c$ and $R_d$, which are identical or different, represent a hydrogen atom or an optionally substituted $(C_1-C_8)$alkyl group, preferentially of $C_1-C_4$, or alternatively $R_c$ contiguous with $W^+$ and/or $R_d$ contiguous with Ar form, with the atoms that carry them, a (hetero)cycloalkyl; particularly, $R_c$ is contiguous with $W^+$ and they form a (hetero)cycloalkyl such as cyclohexyl;
- $Q^-$ is an organic or inorganic anionic counterion as defined previously.

Among the natural direct dyes that can be used according to the invention, mention may be made of lawsone, juglone, alizarin, purpurin, carminic acid, kermesic acid, purpurogallin, protocatechualdehyde, indigo, isatin, curcumin, spinulosin, apigenidin and orceins. Extracts or decoctions containing these natural dyes and in particular cataplasms or henna-based extracts may also be used.

The direct dye(s) more particularly represent from 0.001% to 10% by weight and preferably from 0.005% to 5% by weight of the total weight of the composition.

One or more oxidation dyes can be combined with the direct dyes. The oxidation dyes are generally chosen from one or more oxidation bases optionally combined with one or more couplers.

The composition and the method according to the invention comprise a) one or more oxidation dyes and b) optionally one or more direct dyes or their mixtures of a) and b) which will be described in detail below.

The oxidation dye(s) are chosen from one or more oxidation bases optionally combined with one or more couplers.

Among the para-phenylenediamines that may be mentioned, for example, are para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and addition salts thereof.

Among the para-phenylenediamines mentioned above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and addition salts thereof, are particularly preferred.

Among the bis(phenyl)alkylenediamines that may be mentioned, for example, are N,N'-bis((3-hydroxyethyl)-N,N'-bis (4'-aminophenyl)-1,3-diaminopropanol, N,N'-bis((3-hydroxyethyl)-N,N'-bis(4'-aminophenyl)ethylenediamine, N,N'-bis(4-aminophenyl)-tetramethylenediamine, N,N'-bis((3-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-((β-hydroxyethyl)aminomethyl)phenol and 4-amino-2-fluorophenol, and addition salts thereof.

Among the ortho-aminophenols that may be mentioned, for example, are 2-aminophenol, 2-amino-5-methylphenol, 2-amino-6-methylphenol and 5-acetamido-2-aminophenol, and addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in Patents GB 1 026 978 and GB 1 153 196, for instance 2,5-diaminopyridine, 2-(4-methoxyphenyl)amino-3-aminopyridine and 3,4-diaminopyridine, and addition salts thereof.

Other pyridine oxidation bases of use in the present invention are the 3-aminopyrazolo[1,5-a]pyridine oxidation bases or the addition salts thereof described, for example, in Patent Application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and addition salts thereof.

Among the pyrimidine derivatives that may be mentioned are the compounds described, for example, in Patents DE 2359399, JP 88-169571, JP 05-63124 and EP 0 770 375 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and addition salts thereof, and tautomeric forms thereof, when a tautomeric equilibrium exists.

Among the pyrazole oxidation bases that may be mentioned are the compounds described in Patents DE 3 843 892 and DE 4 133 957 and Patent Applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole and 3,5-diamino-4-(β-hydroxyethyl)amino-1-methylpyrazole, and addition salts thereof. Use may also be made of 4,5-diamino-1-(β-methoxyethyl)pyrazole.

A 4,5-diaminopyrazole will preferably be used as pyrazole compound, and even more preferentially 4,5-diamino-1-(R-hydroxyethyl)pyrazole and/or one of the addition salts thereof.

The composition according to the invention may optionally comprise one or more couplers advantageously chosen from those conventionally used in the dyeing of keratin fibres.

Among these couplers, mention may be made especially of meta-phenylenediamines, meta-aminophenols, meta-diphenols, naphthalene couplers and heterocyclic couplers, and also addition salts thereof.

Mention may be made, for example, of 1,3-dihydroxybenzene, 1,3-dihydroxy-2-methylbenzene, 4-chloro-1,3-dihydroxybenzene, 2,4-diamino-1-(6-hydroxyethyloxy)benzene, 2-amino-4-(6-hydroxyethylamino)-1-methoxybenzene, 1,3-diaminobenzene, 1,3-bis(2,4-diaminophenoxy)propane, 3-ureidoaniline, 3-ureido-1-(dimethylamino)benzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(6-hydroxyethyl)amino-3,4-methylenedioxybenzene, 2,6-bis(6-hydroxyethylamino)toluene, 6-hydroxyindoline, 2,6-dihydroxy-4-methylpyridine, 1H-3-methyl pyrazol-5-one, 1-phenyl-3-methylpyrazol-5-one, 2,6-dimethylpyrazolo[1,5-b][1,2,4]triazole, 2,6-dimethyl-[3,2-c][1,2,4]triazole and 6-methylpyrazolo[1,5-a]benzimidazole, addition salts thereof, and mixtures thereof.

In general, the addition salts of the oxidation bases and couplers that may be used in the context of the invention are especially chosen from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the composition and of the ready-for-use composition.

The coupler(s), if they are present, each advantageously represent from 0.001% to 10% by weight relative to the total weight of the composition, and preferably from 0.005% to 5% by weight relative to the total weight of the composition and of the ready-for-use composition.

According to a preferred embodiment of the invention, the oxidation bases are other than pyrazolones.

The composition according to the invention may optionally comprise b) one or more synthetic or natural dyes chosen from ionic and non-ionic entities, preferably cationic or non-ionic entities, either as sole dyes or in addition to the oxidation dye(s).

Mention may be made, as examples of suitable direct dyes, of the direct dyes as defined previously.

Among the natural dyes that can be used according to the invention, mention may be made of lawsone, juglone, alizarin, purpurin, carminic acid, kermesic acid, purpurogallin, protocatechualdehyde, indigo, isatin, curcumin, spinulosin, apigenidin and orceins. Extracts or decoctions containing these natural dyes and in particular cataplasms or henna-based extracts may also be used.

When they are present, the direct dye(s) more particularly represent from 0.001% to 10% by weight and preferably from 0.005% to 5% by weight of the total weight of the composition.

According to a preferred embodiment of the invention, the method is a dyeing method and the composition comprises at least one dye and preferably at least one oxidation dye as defined previously and is devoid of direct dye.

According to another preferred embodiment of the invention, the composition comprising at least one direct dye as defined previously is devoid of oxidation dye.

According to yet another specific embodiment, the dyeing method and the composition according to the invention employ at least one direct dye and at least one oxidation dye.

v) The basifying agents:

The composition of the invention and the method of the invention can additionally comprise v) one or more basifying agents. The basifying agent(s) may be inorganic or organic or hybrid.

The inorganic basifying agent(s) are preferably chosen from aqueous ammonia, alkali metal carbonates or bicarbonates such as sodium carbonate, potassium carbonate, sodium bicarbonate or potassium bicarbonate, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it is the $pK_b$ corresponding to the functional group of highest basicity. In addition, the organic amines do not comprise any alkyl or alkenyl fatty chains comprising more than ten carbon atoms.

The organic basifying agent(s) are chosen, for example, from alkanolamines, oxyethylenated and/or oxypropylenated ethylenediamines, amino acids and the compounds of formula (VI) below:

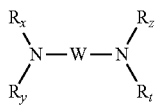
(VI)

in which formula (VI) W is a divalent $C_1$-$C_6$ alkylene radical optionally substituted by one or more hydroxyl groups or a $C_1$-$C_6$ alkyl radical, and/or optionally interrupted by one or more heteroatoms such as 0, or $NR_u$, and $R_x$, $R_y$, $R_z$, $R_t$ and $R_u$, which are identical or different, represent a hydrogen atom or a $C_1$-$C_6$ alkyl, $C_1$-$C_6$ hydroxyalkyl or $C_1$-$C_6$ aminoalkyl radical.

Examples of amines of formula (VI) that may be mentioned include 1,3-diaminopropane, 1,3-diamino-2-propanol, spermine and spermidine.

The term "alkanolamine" means an organic amine comprising a primary, secondary or tertiary amine functional group and one or more linear or branched $C_1$-$C_8$ alkyl groups carrying one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for implementing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that can be used are of natural or synthetic origin, in their L, D or racemic form, and comprise at least one acid functional group chosen more particularly from carboxylic acid, sulfonic acid, phosphonic acid or phosphoric acid functional groups. The amino acids may be in neutral or ionic form.

As amino acids that can be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine functional group optionally included in a ring or in a ureido functional group.

Such basic amino acids are preferably chosen from those corresponding to the formula (VII) below:

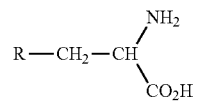
(VII)

in which formula (VII) R represents a group chosen from:

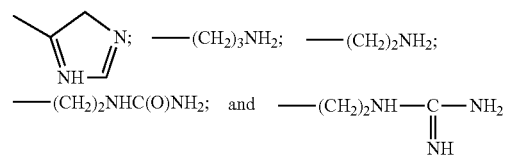

The compounds corresponding to formula (VII) are histidine, lysine, arginine, ornithine and citrulline.

The organic amine may also be chosen from organic amines of heterocyclic type. Besides histidine, which has already been mentioned in the amino acids, mention may in particular be made of pyridine, piperidine, imidazole, triazole, tetrazole and benzimidazole.

The organic amine may also be chosen from amino acid dipeptides. As amino acid dipeptides that can be used in the present invention, mention may be made especially of carnosine, anserine and balenine.

The organic amine may also be chosen from compounds comprising a guanidine functional group. As amines of this type that can be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the basifying agent(s) present in the composition of the invention are chosen from aqueous ammonia, alkanolamines, amino acids in neutral or ionic form, in particular basic amino acids, and preferably corresponding to those of formula (VII).

More preferably still, the basifying agent(s) are chosen from aqueous ammonia and alkanolamines, such as monoethanolamine (MEA), and better still from alkanolamines, such as monoethanolamine (MEA).

Advantageously, the composition according to the invention has a content of basifying agent(s) ranging from 0.01% to 30% by weight and preferably from 0.1% to 20% by weight relative to the weight of the composition.

vii) Chemical Oxidizing Agent

The composition of the invention may also comprise vi) one or more chemical oxidizing agents. The expression "chemical oxidizing agent" is understood to mean an oxidizing agent other than atmospheric oxygen. The composition of the invention preferably contains one or more chemical oxidizing agents.

More particularly, the chemical oxidizing agent(s) are chosen from hydrogen peroxide, urea hydrogen peroxide, alkali metal bromates, peroxygenated salts, for instance persulfates or perborates, peracids and precursors thereof and alkali metal or alkaline earth metal percarbonates.

This oxidizing agent is advantageously formed from hydrogen peroxide and especially in aqueous solution (aqueous hydrogen peroxide solution), the concentration of which may vary more particularly from 0.1% to 50% by weight, more preferably still from 0.5% to 20% by weight and better still from 1% to 15% by weight relative to the weight of the composition.

Preferably, the composition of the invention does not contain any peroxygenated salts.

Substantive Polymer

According to a specific embodiment of the invention, the composition contains at least one substantive polymer, in particular a cationic polymer. For the purposes of the present invention, the term "cationic polymer" denotes any polymer containing cationic groups and/or groups that can be ionized to give cationic groups.

The cationic polymers that may be used in accordance with the present invention may be chosen from any of those already known per se as improving the cosmetic properties of the hair, namely, especially, those described in Patent Application EP-A-337 354 and in French Patents FR-2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or be carried by a side substituent directly attached thereto.

The cationic polymers used generally have a number-average molecular weight of between 500 and $5 \times 10^6$ approximately and preferably of between $10^3$ and $3 \times 10^6$ approximately.

Among the cationic polymers that may be mentioned more particularly are polymers of the polyamine, polyaminoamide and polyquaternary ammonium type.

These are known products. They are described in particular in French Patents 2 505 348 and 2 542 997. Among said polymers, mention may be made of: (1) Homopolymers or copolymers derived from acrylic or methacrylic esters or amides and comprising at least one of the units of formula (A), (B), (C) or (D) below:

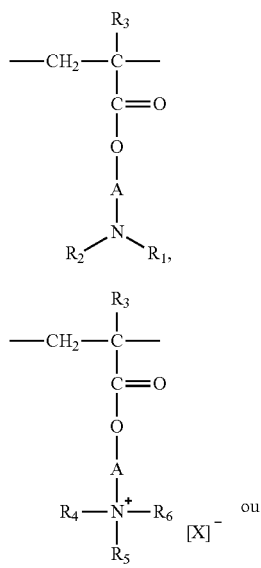

(A)

(B)

-continued

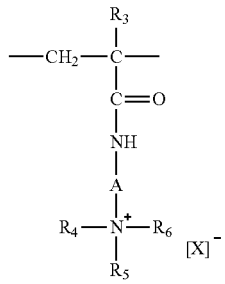

(C)

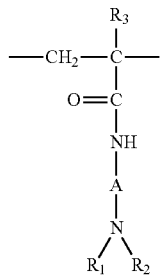

(D)

in which formula (A), (B), (C) or (D):

$R_3$, which are identical or different, denote a hydrogen atom or a $CH_3$ radical;

A, which are identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which are identical or different, represent an alkyl group containing from 1 to 18 carbon atoms or a benzyl radical and preferably an alkyl group containing from 1 to 6 carbon atoms;

$R_1$ and $R_2$, which are identical or different, represent hydrogen or an alkyl group containing from 1 to 6 carbon atoms, and preferably methyl or ethyl;

X denotes an anionic counterion derived from an inorganic or organic acid, such as a methosulfate anion or a halide such as chloride or bromide.

The polymers of family (1) can also contain one or more units deriving from comonomers which may be chosen from the family of acrylamides, methacrylamides, diacetone acrylamides, acrylamides and methacrylamides substituted on the nitrogen by lower ($C_1$-$C_4$)alkyls, acrylic or methacrylic acids or esters thereof, vinyllactams such as vinylpyrrolidone or vinylcaprolactam, and vinyl esters.

Thus, among these polymers of family (1), mention may be made of:

copolymers of acrylamide and of dimethylaminoethyl methacrylate quaternized with dimethyl sulfate or with a methyl halide, such as that sold under the name Hercofloc by the company Hercules, copolymers of acrylamide and of methacryloyloxyethyltrimethylammonium chloride which are described, for example, in Patent Application EP-A-080 976 and are sold under the name Bina Quat P 100 by the company Ciba Geigy, the copolymer of acrylamide and of methacryloyloxyethyltrimethylammonium methosulfate sold under the name Reten by the company Hercules, quaternized or non-quaternized vinylpyrrolidone/dialkylaminoalkyl acrylate or methacrylate copolymers, such as the products sold under the name Gafquat by the company ISP, such as, for example, Gafquat 734 or Gafquat 755, or alternatively the products known as Copolymer 845, 958 and 937. These polymers are described in detail in French Patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, and quaternized vinylpyrrolidone/dimethylaminopropylmethacrylamide copolymers, such as the product sold under the name Gafquat HS 100 by the company ISP.

(2) Cellulose ether derivatives comprising quaternary ammonium groups described in French Patent 1 492 597, and in particular the polymers sold under the "JR" names (JR 400, JR 125, JR 30M) or "LR" names (LR 400, LR 30M) by the company Union Carbide Corporation. These polymers are also defined in the CTFA dictionary as quaternary ammoniums of hydroxyethyl cellulose that has reacted with an epoxide substituted by a trimethylammonium group.

(3) Cationic cellulose derivatives such as cellulose copolymers or cellulose derivatives grafted with a water-soluble quaternary ammonium monomer, and described in particular in U.S. Pat. No. 4,131,576, such as hydroxyalkyl celluloses, for instance hydroxymethyl, hydroxyethyl or hydroxypropyl celluloses grafted in particular with a methacryloylethyltrimethylammonium, methacrylamidopropyltrimethylammonium or dimethyldiallylammonium salt.

The commercial products corresponding to this definition are more particularly the products sold under the names Celquat L 200 and Celquat H 100 by the company National Starch.

(4) The cationic polysaccharides described more particularly in U.S. Pat. Nos. 3,589,978 and 4,031,307, such as guar gums containing cationic trialkylammonium groups. Guar gums modified by a 2,3-epoxypropyltrimethylammonium salt (e.g. chloride) are used, for example.

Such products are sold in particular under the trade names Jaguar C13 S, Jaguar C 15, Jaguar C 17 or Jaguar C162 by the company Meyhall.

(5) Polymers formed from piperazinyl units and divalent alkylene or hydroxyalkylene radicals containing straight or branched chains, optionally interrupted by oxygen, sulfur or nitrogen atoms or by aromatic or heterocyclic rings, and also the oxidation and/or quaternization products of these polymers. Such polymers are described, in particular, in French Patents 2 162 025 and 2 280 361.

(6) Water-soluble polyaminoamides prepared in particular by polycondensation of an acid compound with a polyamine; these polyaminoamides can be crosslinked by an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively by an oligomer resulting from the reaction of a difunctional compound which is reactive with regard to a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they contain one or more tertiary amine functional groups, quaternized. Such polymers are described, in particular, in French Patents 2 252 840 and 2 368 508.

(7) Polyaminoamide derivatives resulting from the condensation of polyalkylenepolyamines with polycarboxylic acids followed by alkylation by bifunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Such polymers are especially described in French Patent 1 583 363.

Among these derivatives, mention may be made more particularly of the adipic acid/dimethylaminohydroxypropyldiethylenetriamine polymers sold under the name Cartaretine F, F4 or F8 by the company Sandoz.

(8) Polymers obtained by reaction of a polyalkylenepolyamine containing two primary amine groups and at least one secondary amine group with a dicarboxylic acid chosen from diglycolic acid and saturated aliphatic dicarboxylic acids having from 3 to 8 carbon atoms. The molar ratio of the polyalkylenepolyamine to the dicarboxylic acid is between 0.8:1 and 1.4:1; the polyaminoamide resulting therefrom is reacted with epichlorohydrin in a molar ratio of epichlorohydrin relative to the secondary amine group of the polyaminoamide of between 0.5:1 and 1.8:1. 1. Such polymers are described in particular in U.S. Pat. Nos. 3,227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyldiethylenetriamine copolymer.

(9) Cyclopolymers of alkyldiallylamine or of dialkyldiallylammonium, such as the homopolymers or copolymers containing, as main constituent of the chain, units corresponding to the formula (VIII) or (IX):

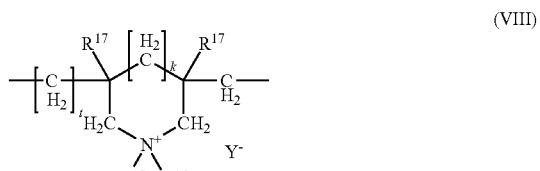

(VIII)

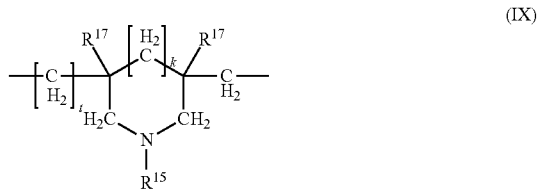

(IX)

in which formula (VIII) or (IX):

k and t are equal to 0 or 1, the sum k+t being equal to 1;

$R^{17}$ denotes a hydrogen atom or a methyl radical;

$R^{15}$ and $R^{16}$ denote, independently of one another, an alkyl group having from 1 to 22 carbon atoms, a hydroxyalkyl group in which the alkyl group preferably has from 1 to 5 carbon atoms, or a lower ($C_1$-$C_4$) amidoalkyl group, or $R^{15}$ and $R^{16}$ can denote, together with the nitrogen atom to which they are attached, heterocyclic groups, such as piperidinyl or morpholinyl;

$Y^-$ is an anionic counterion such as bromide, chloride, acetate, borate, citrate, tartrate, bisulfate, bisulfite, sulfate or phosphate. These polymers are especially described in French Patent 2 080 759 and in its Certificate of Addition 2 190 406.

Among the polymers defined above, mention may be made more particularly of the dimethyldiallylammonium halide (chloride) homopolymer, such as those sold under the name polyquaternium-6 or Merquat 100 by the company Calgon (and its homologues of low weight-average molecular weight), and the copolymers of diallyldimethylammonium halide (chloride) and of acrylamide, such as those sold under the name Merquat 550 or polyquaternium-7.

(10) The diquaternary ammonium polymer containing repeat units corresponding to the formula (X):

in which formula (X):

$R_{18}$, $R_{19}$, $R_{20}$ and $R_{21}$, which are identical or different, represent aliphatic, alicyclic or arylaliphatic radicals comprising from 1 to 20 carbon atoms or lower hydroxyalkyl aliphatic radicals, or else $R_{18}$, $R_{19}$, $R_{20}$ and $R_{21}$, together or separately, form, with the nitrogen atoms to which they are attached, heterocycles optionally comprising a second heteroatom other than nitrogen;

or else $R_{18}$, $R_{19}$, $R_{20}$ and $R_{21}$ represent a linear or branched $C_1$-$C_6$ alkyl radical substituted by a nitrile, ester, acyl, amide or —C(O)—O—$R_{22}$-D or —C(O)—NH—$R_{22}$-D group, where $R_{22}$ is a ($C_1$-$C_6$)alkylene and D is a quaternary ammonium group;

$A_1$ and $B_1$ represent polymethylene groups containing from 2 to 20 carbon atoms, which may be linear or branched and saturated or unsaturated and may contain, bonded to or inserted in the main chain, one or more aromatic rings, or one or more oxygen or sulfur atoms or sulfoxide, sulfone, disulfide, amino, alkylamino, hydroxyl, quaternary ammonium, ureido, amide or ester groups, and X⁻, which are identical or different, denote an anionic counterion derived from an inorganic or organic acid;

$A_1$, $R_{18}$ and $R_{20}$ can form, with the two nitrogen atoms to which they are attached, a piperazine ring; in addition, if $A_1$ denotes a saturated or unsaturated and linear or branched ($C_1$-$C_6$)alkylene or hydroxy($C_1$-$C_6$)alkylene radical, $B_1$ can also denote a —$(CH_2)_n$—C(O)-D-C(O)—$(CH_2)_n$— group in which D denotes:

a) a glycol residue of formula: —O—Z—O—, where Z denotes a linear or branched divalent hydrocarbon radical, such as ($C_1$-$C_6$)alkylene, or a group corresponding to one of the following formulae:

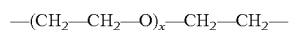

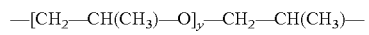

where x and y denote an integer from 1 to 4, representing a defined and unique degree of polymerization, or any number from 1 to 4, representing an average degree of polymerization;

b) a bis-secondary diamine residue such as a piperazine derivative;

c) a bis-primary diamine residue of formula: —NH—Y—NH—, where Y denotes a linear or branched hydrocarbon radical, or alternatively the divalent radical

d) a ureylene group of formula: —NH—C(O)—NH—.

Preferably, X⁻ is a halide anion such as chloride or bromide. These polymers generally have a number-average molecular weight of between 1000 and 100 000.

Polymers of this type are described in particular in French Patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeat units corresponding to the following formula (a):

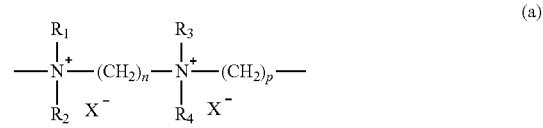

in which formula (a):

$R_1$, $R_2$, $R_3$ and $R_4$, which are identical or different, denote a ($C_1$-$C_4$)alkyl or hydroxy($C_1$-$C_4$)alkyl radical having from 1 to 4 carbon atoms, and n and p are integers varying from 2 to 20 approximately, and X⁻, which is identical or different, is an anionic counterion derived from an inorganic or organic acid, in particular halide;

(11) Polyquaternary ammonium polymers composed of units of formula (XI):

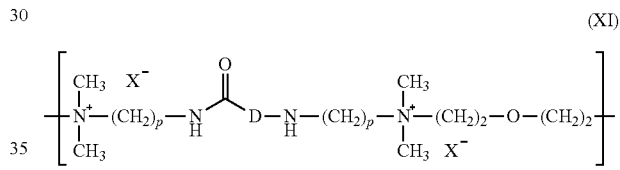

in which formula (XI):

p, which is identical or different, denotes an integer between 1 and 6 inclusive, D represents a bond or a divalent —$(CH_2)_r$—C(O)— group in which r denotes a number equal to 4 or to 7, and X⁻, which is identical or different, is an anionic counterion derived from an inorganic or organic acid, in particular halide.

Cationic polymers comprising units of formula (XI) are especially described in Patent Application EP-A-122 324 and may be prepared according to the processes described in U.S. Pat. Nos. 4,157,388, 4,390,689, 4,702,906 and 4,719,282.

Among these polymers, the ones that are preferred are those for which the molecular weight, measured by carbon-13 NMR, is less than 100 000, and in the formula of which:

p is equal to 3, and a) D represents a —$(CH_2)_4$—CO— group and X⁻ denotes a halide, such as chloride, the molecular weight measured by carbon-13 NMR ($^{13}$C NMR) being about 5600; a polymer of this type is provided by the company Miranol under the name Mirapol-AD1, b) D represents a —$(CH_2)_7$—CO— group and X⁻ denotes a halide, such as chloride, the molecular weight measured by carbon-13 NMR ($^{13}$C NMR) being about 8100; a polymer of this type is provided by the company Miranol under the name Mirapol-AZ1, c) D represents a bond and X⁻ denotes a halide, such as chloride, the molecular weight measured by carbon-13 NMR ($^{13}$C NMR) being about 25 500; a polymer of this type is sold by the company Miranol under the name Mirapol-A15, d) a block copolymer, formed of units corresponding to the polymers described in paragraphs a) and c), provided by the company Miranol under the names Mirapol-9 ($^{13}$C NMR molecular weight, approximately 7800), Mirapol-175 ($^{13}$C NMR molecular weight, approximately 8000) and Mirapol-95 ($^{13}$C NMR molecular weight, approximately 12 500).

Even more particularly, the polymer containing units of formula (VII) in which p is equal to 3, D denotes the value zero and X denotes a chlorine atom, the molecular weight measured by carbon-13 NMR ($^{13}$C NMR) being approximately 25 500, is preferred according to the invention.

(12) Quaternary polymers of vinylpyrrolidone and of vinylimidazole, for instance the products sold under the names Luviquat FC 905, FC 550 and FC 370 by the company BASF.

(13) Polyamines such as Polyquart H sold by Henkel, referred to under the name Polyethylene Glycol (15) Tallow Polyamine in the CTFA dictionary.

(14) The crosslinked polymers of methacryloyloxy($C_1$-$C_4$) alkyl tri($C_1$-$C_4$)alkylammonium salts, such as the polymers obtained by homopolymerization of dimethylaminoethyl methacrylate quaternized by methyl chloride, or by copolymerization of acrylamide with dimethylaminoethyl methacrylate quaternized by methyl chloride, the homo- or copolymerization being followed by crosslinking by an olefinically unsaturated compound, in particular methylenebisacrylamide. A crosslinked acrylamide/methacryloyloxyethyltrimethylammonium chloride copolymer (20/80 by weight) in the form of a dispersion containing 50% by weight of said copolymer in mineral oil can be used more particularly. This dispersion is sold under the name Salcare® SC 92 by the company Allied Colloids. A crosslinked methacryloyloxyethyltrimethylammonium chloride homopolymer containing about 50% by weight of the homopolymer in mineral oil or in a liquid ester may also be used. These dispersions are sold under the names Salcare®SC 95 and Salcare® SC 96 by the company Allied Colloids.

Other cationic polymers that may be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among all the cationic polymers capable of being used in the context of the present invention, it is preferable to employ the polymers of families (9) and (10) and more particularly the polymers of family (10) or of formula (a) are chosen from the polymers of following formulae (W) and (U):

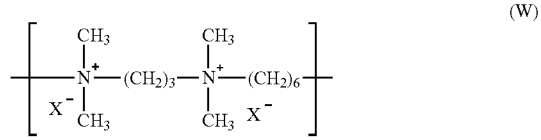

with X⁻ representing a halide, such as chloride;
and especially those for which the molecular weight, determined by gel permeation chromatography, is between 9500 and 9900;

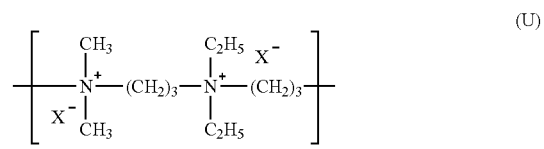

with X⁻ representing a halide, such as bromide;
and in particular those whose molecular weight, determined by gel permeation chromatography, is about 1200.

The composition according to the invention very advantageously comprises at least one cationic polymer chosen from substantive polymers:
- of the type of alkyldiallylamine or dialkyldiallylammonium homopolymers (such as, for example, Merquat 100 or polyquaternium-6, which is a dialkyldiallylammonium halide (chloride) homopolymer, sold by the company Nalco), and also the copolymers of these monomers and of acrylamide (for example, the copolymers of diallyldimethylammonium halide (chloride) and of acrylamide, sold in particular under the name Merquat 550 or polyquaternium-7), and
- the polymers of formula (a) as defined previously and in particular:
    - the polymers with the repeat units of formula (W) as defined previously, in particular those for which the molecular weight, determined by gel permeation chromatography, is between 9500 and 9900;
    - the polymers (U) as defined previously, in particular those for which the molecular weight, determined by gel permeation chromatography, is approximately 1200.

According to a particularly advantageous form of the invention, the composition of the invention comprises at least one cationic substantive polymer which is (W) and/or at least one cyclopolymer of dialkyldiallylammonium of formula (VIII), such as dialkyldiallylammonium halide (chloride) homopolymers.

The concentration of cationic polymer in the compositions according to the present invention may vary from 0.01% to 10% by weight relative to the total weight of the composition, preferably from 0.1% to 5% by weight and more preferably still from 0.2% to 3% by weight relative to the total weight of the composition.

Solvent

The composition according to the invention may also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monoethyl ether and diethylene glycol monomethyl ether; and also aromatic alcohols or ethers, for instance benzyl alcohol or phenoxyethanol, and mixtures thereof.

The solvent(s), if they are present, represent a content usually ranging from 1% to 40% by weight and preferably from 5% to 30% by weight relative to the weight of the composition.

Other Additives

The composition according to the invention may also contain various adjuvants conventionally used in hair dyeing compositions, such as anionic, non-ionic, amphoteric or zwitterionic polymers or mixtures thereof; inorganic thickeners, in particular fillers such as clays or talc; organic thickeners with, in particular, anionic, cationic, non-ionic and amphoteric polymeric associative thickeners; antioxidants; penetrating agents; sequestering agents; fragrances; dispersing agents; film-forming agents; ceramides; preservatives; or opacifying agents.

The above adjuvants are generally present in an amount for each of them of between 0.01% and 20% by weight relative to the weight of the composition.

The composition can comprise in particular one or more fillers or inorganic thickeners, such as organophilic silicas, fumed silicas, clays, in particular organophilic clays, talc, or mixtures thereof.

The fumed silicas can be obtained by high-temperature pyrolysis.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylarylsulfonates and amine oxides, and mixtures thereof.

Organophilic clays that may be mentioned include quaternium-18 bentonites such as those sold under the names Bentone 3, Bentone 38 and Bentone 38V by the company Rheox, Tixogel VP by the company United Catalyst, Claytone 34, Claytone 40 and Claytone XL by the company Southern Clay; stearalkonium bentonites such as those sold under the names Bentone 27 by the company Rheox, Tixogel LG by the company United Catalyst and Claytone AF and Claytone APA by the company Southern Clay; and quaternium-18/benzalkonium bentonites such as those sold under the names Claytone HT and Claytone PS by the company Southern Clay.

The fumed silicas may be obtained by high-temperature pyrolysis of a volatile silicon compound in an oxyhydrogen flame, producing a finely divided silica. This process makes it possible especially to obtain hydrophilic silicas having a large number of silanol groups at their surface. Such hydrophilic silicas are sold, for example, under the names Aerosil 130®, Aerosil 200®, Aerosil 255®, Aerosil 300® and Aerosil 380® by the company Degussa, and Cab-O-Sil HS-5®, Cab-O-Sil EH-5®, Cab-O-Sil LM-130®, Cab-0-Sil MS-55® and Cab-O-Sil M-5® by the company Cabot.

It is possible to chemically modify the surface of the silica via chemical reaction in order to reduce the number of silanol groups. It is especially possible to replace silanol groups with hydrophobic groups: a hydrophobic silica is then obtained.

The hydrophobic groups may be:
trimethylsiloxyl groups, which are obtained especially by treating fumed silica in the presence of hexamethyldisilazane. Silicas thus treated are known as "Silica silylate" according to the CTFA (6th Edition, 1995). They are sold, for example, under the references Aerosil R812® by the company Degussa, and Cab-O-Sil TS-530® by the company Cabot.
dimethylsilyloxyl or polydimethylsiloxane groups, which are especially obtained by treating fumed silica in the presence of polydimethylsiloxane or dimethyldichlorosilane. Silicas thus treated are known as "Silica dimethyl silylate" according to the CTFA (6th Edition, 1995). They are sold, for example, under the references Aerosil R972® and Aerosil R974® by the company Degussa, and Cab-O-Sil TS-610® and Cab-O-Sil TS-720® by the company Cabot.

The fumed silica preferably has a particle size that may be nanometric to micrometric, for example ranging from about 5 to 200 nm.

When it is present, the inorganic thickener represents from 1% to 30% by weight relative to the weight of the composition.

The composition can also comprise one or more organic thickeners other than the non-ionic ethers of polyoxyalkylenated fatty alcohols i) described previously.

These thickeners may be chosen from fatty acid amides (coconut diethanolamide or monoethanolamide, oxyethylenated alkyl ether carboxylic acid monoethanolamide), polymeric thickeners such as cellulose-based thickeners (hydroxyethylcellulose, hydroxypropylcellulose or carboxymethylcellulose), guar gum and derivatives thereof (hydroxypropyl guar), gums of microbial origin (xanthan gum or scleroglucan gum), the crosslinked acrylic acid homopolymers for which the INCI name is Carbomer, such as, for example, the polymers sold by the company Lubrizol under the names Carbopol 980, Carbopol 981 and Carbopol Ultrez 10, acrylate/$C_{10}$-$C_{30}$-alkylacrylate copolymers (INCI name: Acrylates/$C_{10}$-$C_{30}$ Alkyl Acrylate Crosspolymer) such as the products sold by the company Lubrizol under the trade names Pemulen TR1, Pemulen TR2, Carbopol 1382 and Carbopol EDT 2020, optionally crosslinked acrylamidopropanesulfonic acid homopolymers or copolymers, and associative polymers (polymers comprising hydrophilic regions and fatty-chain hydrophobic regions (the fatty chain being an alkyl or alkenyl chain comprising at least 10 carbon atoms), which are capable, in an aqueous medium, of reversibly combining with one another or with other molecules).

The content of organic thickener(s), if they are present, usually varies from 0.01% to 20% by weight and preferably from 0.1% to 5% by weight relative to the weight of the composition.

The composition of the invention may be in various forms, for instance a solution, an emulsion (milk or cream) or a gel.

Methods of the Invention

The composition according to the invention comprising the ingredients i) to vi) as defined previously is applied to dry or wet keratin fibres. It is left in place on the fibres for a time generally of from 1 minute to 1 hour and preferably from 5 minutes to 30 minutes.

The temperature during the dyeing process is conventionally between ambient temperature (between 15° C. and 25° C.) and 80° C. and preferably between ambient temperature and 60° C.

After the treatment, the human keratin fibres are optionally rinsed with water, optionally washed with a shampoo and then rinsed with water, before being dried or left to dry.

The composition according to the invention can be prepared by mixing at least two compositions.

In a first variant of the invention, the composition according to the invention comprising the ingredients i) to vi) as defined previously results from the mixing of two compositions:
  a composition (A) comprising iv) at least one oxidation base as defined previously and optionally at least one coupler as defined previously; and v) at least one basifying agent as defined previously; and
  a composition (B) comprising vi) at least one chemical oxidizing agent as defined previously and optionally a substantive polymer, preferably a cationic substantive polymer, such as (W) and/or cyclopolymer of dialkyldiallylammonium of formula (IV);
it being understood that:
at least one of the compositions (A) or (B) comprises t) at least one non-ionic ether of polyoxyalkylenated fatty alcohols, at least one of the compositions (A) or (B) comprises ii) at least one fatty substance as defined previously, and at least one of the compositions (A) or (B) comprises iii) optionally at least one surfactant as defined previously, so that the fatty substance content of the composition according to the invention resulting from the mixing of the compositions (A)+(B) comprises at least 25% of fatty substances.

Preferentially, at least one of the compositions (A) or (B) is aqueous.

More preferentially still, the two compositions (A) and (B) are aqueous.

In another variant of the invention, the composition according to the invention results from the mixing of two compositions:
- a composition (A) comprising iv) at least one direct dye as defined previously; and v) optionally at least one basifying agent as defined previously; and
- a composition (B) comprising vi) at least one chemical oxidizing agent as defined previously and optionally a substantive polymer, preferably a cationic substantive polymer, such as (W) and/or cyclopolymer of dialkyldiallylammonium of formula (IV);

it being understood that:
at least one of the compositions (A) or (B) comprises i) at least one non-ionic ether of polyoxyalkylenated fatty alcohols and ii) at least one fatty substance as defined previously, and iii) optionally at least one surfactant as defined previously, so that the fatty substance content of the composition according to the invention resulting from the mixing of the compositions (A)+(B) comprises at least 25% of fatty substances.

Preferentially, at least one of the compositions (A) or (B) is aqueous.

More preferentially still, the two compositions (A) and (B) are aqueous.

According to a particularly form for this first variant, the composition (A) comprises the ingredients i) to v) as defined previously and the composition (B) contains the ingredient vi) and can contain it) and a substantive polymer.

The term "aqueous composition" is understood to mean a composition comprising at least 5% water. Preferably, an aqueous composition comprises more than 10% by weight of water and more advantageously still more than 20% by weight of water.

Preferably, the composition (A) is aqueous.

In this variant, the composition (A) comprises at least 50% of fatty substances and more preferably still at least 50% of fatty substances that are liquid at ambient temperature (25° C.).

Preferably, the composition (A) is a direct or inverse emulsion and preferably a direct (O/W) emulsion.

In this variant, the compositions (A) and (B) are preferably mixed in a weight ratio (A)/(B) ranging from 0.2 to 10 and better still from 0.5 to 2.

In a second variant of the invention, the composition according to the invention comprising the ingredients i) to vi) as defined previously results from the mixing of three compositions, the three compositions being aqueous or at least one of them being anhydrous.

More particularly, for the purposes of the invention, the expression "anhydrous cosmetic composition" means a cosmetic composition with a water content of less than 5% by weight, preferably less than 2% by weight and more preferably still less than 1% by weight relative to the weight of said composition. It should be noted that the water present in the composition is more particularly "bound water", such as the water of crystallization of the salts or traces of water absorbed by the starting materials used in the preparation of the compositions according to the invention.

According to this second variant, use will preferably be made of two aqueous compositions (B') and (C') and an anhydrous composition (A'). The anhydrous composition (A') then preferably comprises i) at least one fatty substance as defined previously and more preferably at least one liquid fatty substance. The composition (B') then preferably comprises iv) at least one direct dye and/or at least one oxidation base and optionally at least one coupler as are defined previously. The composition (C') then preferably comprises vi) at least one chemical oxidizing agent as defined previously. The basifying agent(s) (v) as defined previously are optionally included in the compositions (A') and/or (B') and preferably solely in the composition (B'). The surfactant(s) as defined previously are optionally included in at least one of the compositions (A'), (B') or (C'), these three compositions being such that the fatty substance content of the composition according to the invention resulting from the mixing of the three compositions (A')+(B')+(C') comprises at least 25% of fatty substances.

In this variant, the compositions (A'), (B') and (C') are preferably mixed in a weight ratio (A')+(B')/(C') ranging from 0.2 to 10 and better still from 0.5 to 2 and in a weight ratio (A')/(B') ranging from 0.5 to 10 and better still from 1 to 5.

Finally, the invention relates to a first multi-compartment device comprising a first compartment containing the composition (A) as described previously and at least a second compartment containing the composition (B) as described previously, the compositions of the compartments being intended to be mixed before application to give the formulation after mixing according to the invention, provided that the amount of fatty substance in this formulation represents at least 25% by weight relative to the weight of the formulation resulting from the mixing of (A)+(B).

The invention also relates to a second multi-compartment device comprising a first compartment containing the composition (A') as described previously and a second compartment containing a cosmetic composition (B') as described previously and at least a third compartment comprising the composition (C') as described above, the compositions of the compartments being intended to be mixed before application to give the formulation after mixing according to the invention, provided that the amount of fatty substance in this formulation represents at least 25% by weight relative to the weight of the formulation resulting from the mixing of (A')+(B')+(C').

The examples that follow serve to illustrate the invention without, however, being limiting in nature.

EXAMPLES

The following compositions are prepared in which the amounts are expressed in grams of active materials.
Composition A1:

| Ingredients | A1 |
| --- | --- |
| Ceteareth-60 myristyl glycol (Elfacos GT 282 S from AKZO) (non-ionic ether of polyoxyalkylenated fatty alcohol) i) | 0.01 |
| Liquid petroleum jelly (fatty substance) ii) | 60 |
| Cetyl palmitate (fatty substance) ii) | 2 |
| $C_{20}$-$C_{22}$ alcohols (fatty substance) ii) | 4.60 |
| Ethanolamine (basifying agent) v) | 4.46 |
| Oleth-10 (surfactant) iii) | 1 |
| Oleth-20 (surfactant) iii) | 4 |
| Deceth-5 (surfactant) iii) | 1.08 |
| Basic Yellow 87 (dye) iv) | 0.30 |
| Basic Orange 31 (dye) iv) | 0.23 |

| Ingredients | A1 |
| --- | --- |
| Ascorbic acid | 0.25 |
| Glycerol | 5 |
| EDTA | 0.20 |
| Sodium metabisulfite | 0.45 |
| Carbomer (Carbopol 980 from Lubrizol) | 0.10 |
| Water | q.s. for 100 |

Composition B1 (Chemical Oxidizing Agent):

| Ingredients | B1 |
| --- | --- |
| Hydrogen peroxide vi) | 6 |
| Tocopherol | 0.10 |
| Sodium stannate | 0.04 |
| BHT | $1.23 \times 10^{-3}$ |
| Pentasodium pentetate | 0.06 |
| Polyquaternium-6 | 0.2 |
| Dialkyldiallylammonium halide (chloride) homopolymer | |
| Glycerol | 0.5 |
| Cetearyl alcohol | 6 |
| Hexadimethrine chloride (polymer W) | 0.15 |
| Tetrasodium pyrophosphate | 0.03 |
| Liquid petroleum jelly (fatty substance) ii) | 20 |
| PEG-4 Rapeseedamide | 1.20 |
| Steareth-20 (surfactant) iii) | 5 |
| Water | q.s. for 100 |

Application Method:
The 2 compositions A1 and B1 are mixed at the time of use in the following proportions: 10 g of the composition A1+10 g of the composition B1 are applied to locks of grey hair comprising 90% white hairs, in a proportion of 10 g of A1+B1 mixture per 1 g of hair, for 30 minutes.
The hair is then rinsed, washed with a standard shampoo and dried.
The colouration obtained is coppery.

Composition A2:

| Ingredients | A2 |
| --- | --- |
| Ceteareth-60 myristyl glycol (Elfacos GT 282 S from AKZO) (non-ionic ether of polyoxyalkylenated fatty alcohol) i) | 0.01 |
| Liquid petroleum jelly (fatty substance) ii) | 60 |
| Cetyl palmitate (fatty substance) ii) | 2 |
| $C_{20}$-$C_{22}$ alcohols (fatty substance) ii) | 4.60 |
| Ethanolamine (basifying agent) v) | 4.47 |
| Oleth-10 (surfactant) iii) | 1 |
| Oleth-20 (surfactant) iii) | 4 |
| Deceth-5 (surfactant) iii) | 1.08 |
| Resorcinol (dye) iv) | 0.61 |
| m-Aminophenol (dye) iv) | 0.11 |
| 2,4-Diaminophenoxyethanol hydrochloride (dye) iv) | 0.018 |
| Toluene-2,5-diamine (dye) iv) | 0.70 |
| Hydroxybenzomorpholine | 0.03 |
| Ascorbic acid | 0.25 |
| Glycerol | 5 |
| EDTA | 0.20 |
| Sodium metabisulfite | 0.45 |
| Carbomer (Carbopol 980 from Lubrizol) | 0.098 |
| Water | q.s. for 100 |

Composition B2 (chemical oxidizing agent):

| Ingredients | B2 |
| --- | --- |
| Hydrogen peroxide vi) | 6 |
| Tocopherol | 0.10 |
| Sodium stannate | 0.04 |
| Pentasodium pentetate | 0.06 |
| Polyquaternium-6 | 0.2 |
| Dialkyldiallylammonium halide (chloride) homopolymer | |
| Glycerol | 0.5 |
| Cetearyl alcohol (fatty substance) ii) | 6 |
| Hexadimethrine chloride (polymer W) | 0.15 |
| Tetrasodium pyrophosphate | 0.03 |
| Liquid petroleum jelly (fatty substance) ii) | 20 |
| PEG-4 Rapeseedamide | 1.20 |
| Steareth-20 (surfactant) iii) | 5 |
| Preservative | q.s. |
| Water | q.s. for 100 |

Application Method:
The 2 compositions A2 and B2 are mixed at the time of use in the following proportions: 10 g of the composition A2+10 g of the composition B2 are applied to locks of grey hair comprising 90% white hairs, in a proportion of 10 g of A2+B2 mixture per 1 g of hair, for 30 minutes at ambient temperature.
The hair is then rinsed, washed with a standard shampoo and dried.
The hair colouration obtained is light chestnut.

Comparative Tests
Composition 1 (g %)

| Ingredients | Compound 1 |
| --- | --- |
| Disteardimonium hectorite | 3 |
| Octyldodecanol | 11.5 |
| Glycol distearate | 8 |
| Liquid petroleum jelly | 64.5 |
| Propylene carbonate | 1 |
| Laureth-2 | 1 |
| Polysorbate 20 | 11 |

Compositions 2 and 2' (g %)

| Ingredients | *Compound 2 | Compound 2' |
| --- | --- | --- |
| Ceteareth-60 myristyl glycol (Elfacos GT 282 S) | — | 0.5 |
| Pentasodium pentetate | 1 | 1 |
| Sodium metabisulfite | 0.7 | 0.7 |
| Monoethanolamine | 14.5 | 14.5 |
| 2,5-Toluenediamine | 2.25 | 2.25 |
| 2,4-Diaminophenoxyethanol hydrochloride | 0.05 | 0.05 |
| Resorcinol | 2 | 2 |
| m-Aminophenol | 0.36 | 0.36 |
| Hydroxyethyl cellulose | 1.5 | 1.5 |
| Hexylene glycol | 3 | 3 |
| Dipropylene glycol | 3 | 3 |
| Ethanol | 8.25 | 8.25 |
| Propylene glycol | 6.2 | 6.2 |
| Ascorbic acid | 0.25 | 0.25 |
| Water | qs 100 | qs 100 |

*relative to EP 2 198 927, Example 2

Composition 3 (g %)

| Ingredients | Compound 3 |
| --- | --- |
| 50% Aqueous hydrogen peroxide solution | 12 |
| Pentasodium pentetate | 0.15 |
| Sodium stannate | 0.04 |
| Phosphoric acid | qs pH 2.2 |
| Tetrasodium pyrophosphate | 0.03 |
| Liquid petroleum jelly | 20 |

-continued

| Ingredients | Compound 3 |
|---|---|
| Hexadimethrine chloride | 0.15 am |
| Polyquaternium-6 | 0.2 am |
| Glycerol | 0.5 |
| Cetearyl alcohol | 8 |
| Oxyethylenated cetearyl alcohol (33 EO) | 3 |
| Oxyethylenated rapeseed fatty acid amide (4 EO) | 1.2 am |
| Vitamin E | 0.1 |
| Water | qs 100 |

10 g of composition 1+4 g of composition 2 or 2'+16 g of composition 3 are mixed together at the time of use.

Each of the mixtures is then applied to locks of hair containing natural grey hair which are 90% white (NW) hair and permanent-waved grey which are 90% white (PW) hair, in a proportion of 10 g of mixture per 1 g of hair.

After a leave-on time of 30 minutes at room temperature, the hair is rinsed, washed with a standard shampoo and dried.

Color Determination

The colorimetric measurements were carried out using a DATACOLOR SF600X spectrocolorimeter (illuminant D65, angle 10°, specular component included) in the CIELab system.

$L^*$ represents the lightness; the lower the value of $L^*$, the more intense the colouring obtained.

According to this system, L indicates the lightness. The lowest is the value of L, the most intense is the color of the hair. The chromaticity coordinates are expressed by the parameters $a^*$ and $b^*$, $a^*$ indicating the axis of red/green shades and b the axis of yellow/blue shades.

Selectivity of the Coloration

The selectivity of the coloration is the variation of the color between natural colored hair and permed colored hair. Natural hair is representative of the nature of the hair at the point hair and the permed hair is representative of the nature of the hair at the root.

The selectivity is measured by:

$\Delta E$, which is the color variation between a natural colored lock and a permed colored lock, is obtained from the following formula:

$$\Delta E = \sqrt{(L^*-L_o^*)^2+(a^*-a_o^*)^2+(b^*-b_o^*)^2}$$

wherein $L^*$ indicates lightness and $a^*$ and $b^*$ are the chromaticity coordinates of the natural colored locks whereas $L_o^*$ indicates the lightness and $a_o^*$ et $b_o^*$ are the chromaticity of the permed colored locks. The lowest is the value of $\Delta E$, the weakest the selective is the coloration and the best is the color of the hair.

Dyeing Properties:

The selectivity is represented by the colour difference $\Delta E$ between the natural and permanent-waved dyed locks: the lower the value of $\Delta E$, the lower, and therefore better, the selectivity.

| Mixture | Hair type | $L^*$ | $a^*$ | $b^*$ | $\Delta E$ |
|---|---|---|---|---|---|
| 1 + 2 + 3 | NW | 30.12 | 2.99 | 6.95 | 3.90 |
| (comparative) | PW | 26.63 | 2.54 | 5.26 | |
| 1 + 2' + 3 | NW | 23.92 | 2.63 | 4.67 | 1.24 |
| (invention) | PW | 23.39 | 2.45 | 5.78 | |

On natural hair and on permanent-waved hair, the mixture according to the invention results in lower values of $L^*$ compared to the comparative: the colouring obtained with the mixture according to the invention is more intense.

Furthermore, the mixture according to the invention results in a lower value of $\Delta E$ compared to the comparative mixture: the colouring obtained with the mixture according to the invention is significantly less selective thanks to the distinguish feature i.e. the presence of non-ionic ether of polyoxyalkylenated fatty alcohols.

The invention claimed is:

1. A composition for dyeing keratin fibers, comprising:
   i) at least one non-ionic ether of polyoxyalkylenated fatty alcohols of formula (I):

R—(O-Alk)$_n$-O—R'      (I);

wherein, in formula (I):
   R denotes a saturated or unsaturated, linear or branched $C_{10}$-$C_{30}$ hydrocarbon radical,
   R' denotes a saturated or unsaturated, linear or branched $C_{10}$-$C_{30}$ hydrocarbon radical, optionally substituted with at least one hydroxyl radical,
   n is an integer ranging from 1 to about 100, inclusive, and
   Alk is chosen from a linear or branched ($C_1$-$C_6$)alkylene group, ethylene, or propylene,
   ii) at least one fatty substance, wherein the at least one fatty substance is not chosen from oxyalkylenated fatty alcohols,
   iii) optionally at least one surfactant other than i),
   iv) at least one dye chosen from direct dyes and oxidation dyes,
   v) optionally at least one basifying agent, and
   vi) optionally at least one chemical oxidizing agent,
   wherein the at least one fatty substance is present in an amount of at least about 25% by weight, relative to the total weight of the composition.

2. The composition according to claim 1, wherein the at least one non-ionic ether of polyoxyalkylenated fatty alcohol is chosen from the compounds of formula (I) wherein R and R', independently of each other, denote a saturated or unsaturated, linear or branched, $C_{12}$-$C_{20}$ hydrocarbon radical, R' optionally being substituted by at least one hydroxyl radical, and
   wherein n denotes an integer greater than or equal to 20.

3. The composition according to claim 2, wherein n denotes an integer ranging from 40 to 80.

4. The composition according to claim 1, wherein the at least one non-ionic ether of polyoxyalkylenated fatty alcohol is chosen from the compounds of formula (I) wherein R denotes a $C_{16}$-$C_{18}$ alkyl radical, and R' denotes a $C_{14}$ alkyl radical substituted by an —OH group, and
   wherein n is equal to 60.

5. The composition according to claim 1, wherein the at least one non-ionic ether of polyoxyalkylenated fatty alcohol is present in an amount ranging from about 0.001% to about 10% by weight, relative to the total weight of the composition.

6. The composition according to claim 1, wherein the at least one non-ionic ether of polyxyalkylenated fatty alcohol is present in an amount ranging from about 0.001% to about 5% by weight, relative to the total weight of the composition.

7. The composition according to claim 1, wherein the at least one fatty substance ii) is chosen from $C_6$-$C_{16}$ alkanes; non-silicone oils of mineral, vegetable, animal or synthetic origin; fatty alcohols; fatty acid esters; fatty alcohol esters; non-silicone waxes; silicones; and combinations thereof.

8. The composition according to claim 1, wherein the at least one fatty substance ii) is liquid at a temperature of about 25° C. and a pressure of about 760 mmHg, and is chosen from liquid petroleum jelly, $C_6$-$C_{16}$ alkanes, polydecenes, esters of fatty acids or of fatty alcohols, fatty alcohols, and mixtures thereof.

9. The composition according to claim 1, wherein the concentration of the at least one fatty substance ii) ranges from about 25% to about 80% by weight, relative to the weight of the composition.

10. The composition according to claim 1, comprising at least one surfactant iii) chosen from non-ionic surfactants, mono-oxyalkylenated or polyoxyalkylenated non-ionic surfactants, and combinations thereof.

11. The composition according to claim 1, wherein the at least one dye iv) is chosen from one or more direct dyes chosen from azo direct dyes, (poly)methine dyes, cyanines, hemicyanines, styryl dyes, carbonyl dyes, azine dyes, nitro (hetero)aryl dyes, tri(hetero)arylmethane dyes, porphyrin dyes, phthalocyanine dyes, natural direct dyes, and mixtures thereof.

12. The composition according to claim 1, wherein the at least one dye iv) is chosen from at least one cationic direct dye.

13. The composition according to claim 1, wherein the at least one dye iv) is chosen from at least one hydrazono cationic dye of formulae (II) or (III), or azo cationic dye of formulae (IV) or (V):

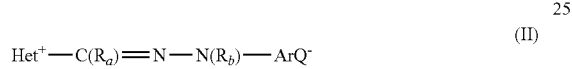

wherein in formulae (II) to (V):
Het$^+$ is chosen from a cationic heteroaryl radical, a heteroaryl radical carrying an endocyclic cationic charge, imidazolium, indolium or pyridinium, which is optionally substituted by at least one $(C_1$-$C_8)$alkyl group;
Ar$^+$ is chosen from an aryl radical, phenyl, or naphthyl, wherein the aryl radical carries an exocyclic cationic charge;
Ar is chosen from a julolidine group, or an aryl group that is optionally substituted by one or more electron-donating groups chosen from i) optionally substituted $(C_1$-$C_8)$ alkyl, ii) optionally substituted $(C_1$-$C_8)$alkoxy, iii) (di)$(C_1$-$C_8)$(alkyl)amino optionally substituted on the alkyl group by a hydroxyl group, iv) aryl$(C_1$-$C_8)$alkylamino, v) optionally substituted N—$(C_1$-$C_8)$alkyl-N-aryl$(C_1$-$C_8)$alkylamino, and combinations thereof;
Ar″ is chosen from a (hetero)aryl group, phenyl, or pyrazolyl, which are optionally substituted by one or more $(C_1$-$C_8)$alkyl, hydroxyl, (di)$(C_1$-$C_8)$(alkyl)amino, $(C_1$-$C_8)$alkoxy or phenyl groups;
$R_a$ and $R_b$, which may be identical or different, represent a hydrogen atom or a $(C_1$-$C_8)$alkyl group, which is optionally substituted; or at least one of $R_a$ with a substituent of Het$^+$ and $R_b$ with a substituent of Ar form, together with the atoms which carry them, a (hetero)cycloalkyl; and
Q$^-$ is chosen from an organic or inorganic anionic counterion, a halide, or an alkyl sulfate.

14. The composition according to claim 13, wherein the at least one cationic direct dye represented by formulae (II) to (V) carries an endocyclic cationic charge.

15. The composition according to claim 1, wherein the at least one dye iv) comprises one or more hydrazono cationic dye of formulae (II-1) and (IV-1) below:

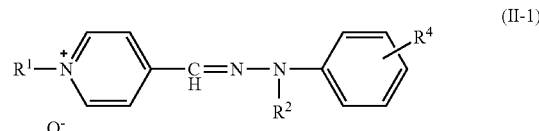
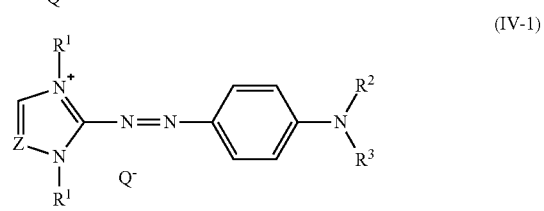

wherein in formulae (II-1) and (IV-1):
$R^1$ is chosen from a $(C_1$-$C_4)$alkyl group or methyl;
$R^2$ and $R^3$, which are identical or different, represent a hydrogen atom, a $(C_1$-$C_4)$alkyl group, or methyl; and
$R^4$ is chosen from a hydrogen atom, an electron-donating group, optionally substituted $(C_1$-$C_8)$alkyl, optionally substituted $(C_1$-$C_8)$alkoxy, or (di)$(C_1$-$C_8)$(alkyl)amino optionally substituted on the alkyl group(s) by a hydroxyl group;
Z is chosen from a —CH group or a nitrogen atom;
Q$^-$ is an anionic counterion, a halide, an alkyl sulfate chloride, methyl sulfate or mesityl.

16. The composition according to claim 1, wherein the at least one dye iv) comprises at least one benzene oxidation base chosen from para-phenylenediamines, bis(phenyl)alkylenediamines, para-aminophenols, ortho-aminophenols, addition salts thereof, and mixtures thereof.

17. The composition according to claim 1, wherein the at least one dye iv) comprises at least one coupler chosen from meta-phenylenediamines, meta-aminophenols, meta-diphenols, naphthalene couplers and heterocyclic couplers.

18. The composition according to claim 1, comprising at least one basifying agent v), wherein the at least one basifying agent is inorganic, organic or hybrid, and is chosen from aqueous ammonia; alkali metal carbonates or bicarbonates; sodium carbonate; sodium bicarbonate; potassium carbonate or potassium bicarbonate; sodium hydroxide or potassium hydroxide; organic amines chosen from alkanolamines, oxyethylenated and/or oxypropylenated ethylenediamines, amino acids, the compounds of formula (VI), and mixtures thereof:

wherein in formula (VI):
W is a divalent $C_1$-$C_6$ alkylene radical optionally substituted by at least one hydroxyl group or a $C_1$-$C_6$ alkyl radical, and/or optionally interrupted by at least one heteroatom such as O, or $N_u$, and
$R_x$, $R_y$, $R_z$, $R_t$ and $R_u$, which are identical or different, are chosen from a hydrogen atom or a $C_1$-$C_6$ alkyl or $C_1$-$C_6$ hydroxyalkyl or $C_1$-$C_6$ aminoalkyl radical.

19. The composition according to claim 1, comprising at least one basifying agent v) chosen from aqueous ammonia, alkanolamines, monoethanolamine, and amino acids in neutral or ionic form.

20. The composition according to claim 1, further comprising at least one cationic substantive polymer chosen from the polymers of the following families:

cyclopolymers of dialkyldiallylammonium, and the homopolymers or copolymers containing, as main constituent of the chain, units corresponding to the formula (VIII):

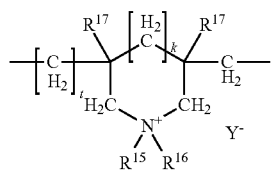

(VIII)

wherein in formula (VIII):
k and t are equal to 0 or 1, the sum k+t being equal to 1;
$R^{17}$ denotes a hydrogen atom or a methyl radical;
$R^{15}$ and $R^{16}$ denote, independently of each other, an alkyl group having from 1 to 22 carbon atoms, a hydroxyalkyl group in which the alkyl group has from 1 to 5 carbon atoms, or a lower ($C_1$-$C_4$) amidoalkyl group, or
$R^{15}$ and $R^{16}$ may optionally denote, together with the nitrogen atom to which they are attached, heterocyclic groups;
$Y^-$ is an anionic counterion;
diquaternary ammonium polymers containing repeat units corresponding to the formula (a) below:

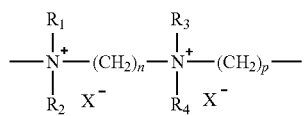

(a)

wherein in formula (a):
$R_1$, $R_2$, $R_3$ and $R_4$, independently of each other, denote a ($C_1$-$C_4$)alkyl or hydroxy($C_1$-$C_4$)alkyl radical having from 1 to 4 carbon atoms,
n and p are integers ranging from 2 to 20, inclusive, and
$X^-$, which may be identical or different, is chosen from anionic counterions derived from an inorganic or organic acid.

21. A method for dyeing keratin fibers, the method comprising applying to said fibers a composition comprising:
i) at least one non-ionic ether of polyoxyalkylenated fatty alcohols of formula (I):

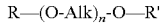   (I);

wherein in formula (I):
R denotes a saturated or unsaturated, linear or branched $C_{10}$-$C_{30}$ hydrocarbon radical,
R' denotes a saturated or unsaturated, linear or branched $C_{10}$-$C_{30}$ hydrocarbon radical, optionally substituted with at least one hydroxyl radical,
n is an integer ranging from 1 to about 100 inclusive, and
Alk is chosen from a linear or branched ($C_1$-$C_6$)alkylene group, ethylene, or propylene,
ii) at least one fatty substance,
iii) optionally at least one surfactant other than i),
iv) at least one dye chosen from direct dyes and oxidation dyes,
v) optionally at least one basifying agent, and
vi) optionally at least one chemical oxidizing agent,
wherein the at least one fatty substance is present in an amount of at least about 25% by weight, relative to the total weight of the composition.

22. The method according to claim 21, wherein the composition is obtained by mixing at least two formulations, including formulation (A) and formulation (B),
wherein formulation (A) comprises:
at least one dye iv) chosen from direct dyes and oxidation dyes, and
optionally at least one basifying agent v); and
wherein formulation (B) comprises:
at least one chemical oxidizing agent vi);
wherein at least one of formulation (A) and formulation (B) comprises the at least one non-ionic ether of polyoxyalkylenated fatty alcohols i) of formula (I), at least one fatty substance ii), and optionally at least one surfactant iii),
wherein the fatty substance content of the composition resulting from the mixing of formulation (A) and formulation (B) is at least about 25% by weight, relative to the total weight of the composition.

23. The method according to claim 22, wherein formulation (A) and formulation (B) are both aqueous, or at least one of formulation (A) and formulation (B) is anhydrous.

24. The method according to claim 22, wherein formulation (A) comprises formulation (A') and formulation (A"),
wherein formulation (A') is anhydrous and comprises at least one fatty substance ii),
wherein formulation (A") comprises at least one dye iv) chosen from direct dyes and oxidation dyes, and
wherein at least one of formulation (A'), formulation (A"), and formulation (B) comprises:
the at least one non-ionic ether of polyoxyalkylenated fatty alcohols i) of formula (I), and
optionally at least one surfactant iii);
wherein optionally at least one of formulation (A') and formulation (A") comprises at least one basifying agent v); and
wherein the fatty substance content of the composition resulting from the mixing of formulation (A'), formulation (A"), and formulation (B) is at least about 25% by weight, relative to the total weight of the composition.

25. A multi-compartment device for implementing a method for dyeing keratin fibers, the method comprising:
applying to said fibers a composition comprising;
i) at least one non-ionic ether of polyoxyalkylenated fatty alcohol of formula (I):

   (I);

wherein in formula (I):
R denotes a saturated or unsaturated, linear or branched $C_{10}$-$C_{30}$ hydrocarbon radical,
R' denotes a saturated or unsaturated, linear or branched $C_{10}$-$C_{30}$ hydrocarbon radical, optionally substituted with at least one hydroxyl radical,
n is an integer ranging from 1 to about 100 inclusive, and
Alk is chosen from a linear or branched ($C_1$-$C_6$)alkylene group, ethylene, or propylene,
ii) at least one fatty substance,
iii) optionally at least one surfactant other than i), iv) at least one dye chosen from direct dyes and oxidation dyes,
v) optionally at least one basifying agent, and
vi) optionally at least one chemical oxidizing agent,
  wherein the at least one fatty substance is present in an amount of at least about 25% by weight relative to the total weight of the composition; and
preparing the composition before the application by mixing at least formulation (A) and formulation (B),
wherein formulation (A) comprises:
  at least one dye iv) chosen from direct dyes and oxidation dyes, and
  optionally at least one basifying agent v); and
wherein formulation (B) comprises:
  at least one chemical oxidizing agent vi);
wherein at least one of formulation (A) and formulation (B) comprises the at least one non-ionic ether of polyoxyalkylenated fatty alcohols i) of formula (I), at least one fatty substance ii), and optionally at least one surfactant iii),
wherein the fatty substance content of the composition resulting from the mixing of formulation (A) and formulation (B) is at least about 25% by weight, relative to the total weight of the composition,
the multi-compartment device comprising:
  a first compartment for containing formulation (A), and
  at least a second compartment for containing the formulation (B).

26. The multi-compartment device according to claim 25,
wherein formulation (A) comprises formulation (A') and formulation (A"),
wherein formulation (A') is anhydrous and comprises at least one fatty substance ii),
wherein formulation (A") comprises at least one dye iv) chosen from direct dyes and oxidation dyes, and
wherein at least one of formulation (A'), formulation (A"), and formulation (B) comprises:
  the at least one non-ionic ether of polyoxyalkylenated fatty alcohols i) of formula (I), and
  optionally at least one surfactant iii);
wherein optionally at least one of formulation (A') and formulation (A") comprises at least one basifying agent v); and
wherein the fatty substance content of the composition resulting from the mixing of formulation (A'), formulation (A"), and formulation (B) is at least about 25% by weight relative to the total weight of the composition;
wherein the first compartment comprises a first subcompartment for containing the formulation (A') and a second subcompartment for containing the formulation (A").

* * * * *

UNITED STATES PATENT AND TRADEMARK OFFICE
CERTIFICATE OF CORRECTION

| | | |
|---|---|---|
| PATENT NO. | : 9,060,944 B2 | Page 1 of 1 |
| APPLICATION NO. | : 14/130800 | |
| DATED | : June 23, 2015 | |
| INVENTOR(S) | : Delphine Charrier et al. | |

It is certified that error appears in the above-identified patent and that said Letters Patent is hereby corrected as shown below:

In the Claims

Claim 18, col. 52, line 60, change "$N_u$" to -- $NR_u$ --.

Signed and Sealed this
Tenth Day of November, 2015

Michelle K. Lee
*Director of the United States Patent and Trademark Office*